US007966866B2

(12) United States Patent
Hansma et al.

(10) Patent No.: US 7,966,866 B2
(45) Date of Patent: Jun. 28, 2011

(54) METHODS AND INSTRUMENTS FOR MATERIALS TESTING

(75) Inventors: Paul Hansma, Goleta, CA (US); Barney Drake, Rena, NV (US); Douglas Rehn, Lompoc, CA (US); Jonathan Adams, Santa Barbara, CA (US); Jason Lulejian, Pismo Beach, CA (US)

(73) Assignee: The Regents of the University of California, Oakland, CA (US)

( * ) Notice: Subject to any disclaimer, the term of this patent is extended or adjusted under 35 U.S.C. 154(b) by 591 days.

(21) Appl. No.: 12/079,444

(22) Filed: Mar. 27, 2008

(65) Prior Publication Data

US 2009/0056427 A1 Mar. 5, 2009

Related U.S. Application Data

(60) Provisional application No. 60/921,788, filed on Apr. 3, 2007.

(51) Int. Cl.
*G01N 3/38* (2006.01)
*G01N 3/317* (2006.01)
(52) U.S. Cl. .......................................................... 73/81
(58) Field of Classification Search ................ 73/81–85; 600/562
See application file for complete search history.

(56) References Cited

U.S. PATENT DOCUMENTS

| 1,770,045 | A |   | 3/1925  | Shore et al. |       |
|-----------|---|---|---------|--------------|-------|
| 2,803,130 | A | * | 8/1957  | Bernhardt    | 73/81 |
| 3,572,097 | A | * | 3/1971  | Kleesattel   | 73/573 |
| 3,956,925 | A | * | 5/1976  | Smith        | 73/81 |
| 4,304,123 | A | * | 12/1981 | Aschinger et al. | 73/81 |
| 4,611,487 | A | * | 9/1986  | Krenn et al. | 73/81 |

(Continued)

OTHER PUBLICATIONS

W.C. Oliver and G.M. Pharr. Measurement of hardness and elastic modulus by instrumented indentation: Advances in understanding and refinements to methodology. J. Mater. Res. 19 (2004), 3.

(Continued)

*Primary Examiner* — John Fitzgerald
(74) *Attorney, Agent, or Firm* — Vista IP Law Group LLP

(57) ABSTRACT

Methods and instruments for characterizing a material, such as the properties of bone in a living human subject, using a test probe constructed for insertion into the material and a reference probe aligned with the test probe in a housing. The housing is hand held or placed so that the reference probe contacts the surface of the material under pressure applied either by hand or by the weight of the housing. The test probe is inserted into the material to indent the material while maintaining the reference probe substantially under the hand pressure or weight of the housing allowing evaluation of a property of the material related to indentation of the material by the probe. Force can be generated by a voice coil in a magnet structure to the end of which the test probe is connected and supported in the magnet structure by a flexure, opposing flexures, a linear translation stage, or a linear bearing. Optionally, a measurement unit containing the test probe and reference probe is connected to a base unit with a wireless connection, allowing in the field material testing.

7 Claims, 27 Drawing Sheets

U.S. PATENT DOCUMENTS

| | | | |
|---|---|---|---|
| 6,068,604 | A | 5/2000 | Krause et al. |
| 6,142,010 | A | 11/2000 | Merck, Jr. |
| 6,247,356 | B1 | 6/2001 | Merck, Jr. et al. |
| 6,405,599 | B1 | 6/2002 | Patt |
| 6,520,004 | B1 * | 2/2003 | Lin .................................. 73/81 |
| 6,983,643 | B2 * | 1/2006 | Brighton et al. .................. 73/81 |
| 7,878,987 | B2 * | 2/2011 | Hansma et al. ................ 600/587 |
| 2002/0170360 | A1 | 11/2002 | Anand et al. |
| 2005/0016264 | A1 * | 1/2005 | Anthe et al. ...................... 73/82 |
| 2005/0113691 | A1 | 5/2005 | Liebschner |
| 2005/0262685 | A1 | 12/2005 | Takaoka et al. |
| 2006/0130566 | A1 * | 6/2006 | Wu ................................... 73/82 |
| 2006/0184251 | A1 | 8/2006 | Zhang et al. |
| 2007/0276292 | A1 * | 11/2007 | Hansma et al. ................ 600/587 |
| 5,305,633 | A * | 4/1994 | Weissenbacher et al. ........ 73/82 |
| 5,373,730 | A * | 12/1994 | Kovacevic ........................ 73/81 |
| 5,450,745 | A | 9/1995 | Flaherty |
| 5,463,897 | A | 11/1995 | Prater |
| 5,473,700 | A | 12/1995 | Fenner, Jr. |
| 5,904,658 | A | 5/1999 | Niederauer et al. |

OTHER PUBLICATIONS

C. A. J. Putman, H. G. Hansma, H. E. Gaub, and P. K. Hansma, Langmuir 8, 3014 (1992).

Briscoe, B.J. and Sebastian, K.S. An analysis of the durometer indentation. Rubber Chemistry and Technology 66 (5): 827-836 1993).

James B. Thompson et al., Nature 414, 774, Dec. 13, 2001.

Paul K. Hansma, Patricia J. Turner, and Georg E. Fantner, Bone Diagnostic Instrument, Review of Scientific Instruments 77, 075105 (2006).

Micro Hardness Tester (MHT) for fracture toughness determination of brittle materials, No. 8, Jul. 1998.

CSM Indentation Testers, four page brochure, Jan. 2009.

ASTM Proposed Instrumented Indentation Testing Standard, pp. 1-4, Oct. 2003.

* cited by examiner

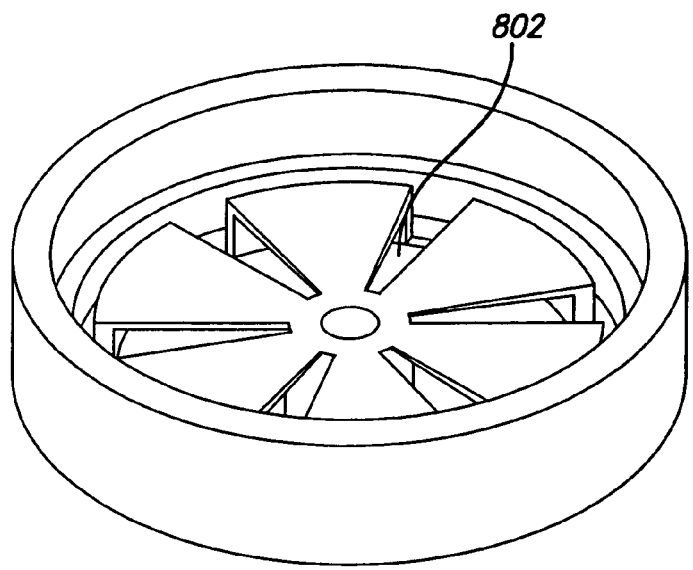
FIG. 8A
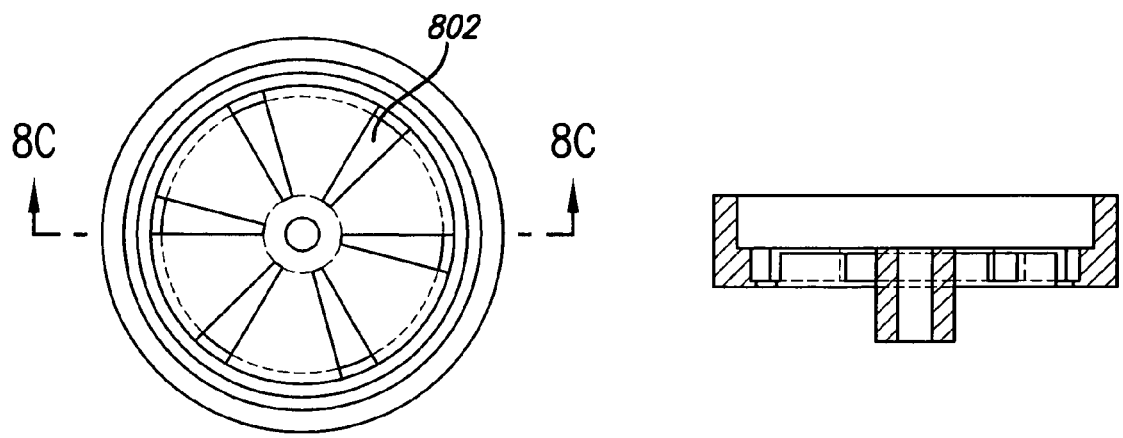
FIG. 8B
FIG. 8C

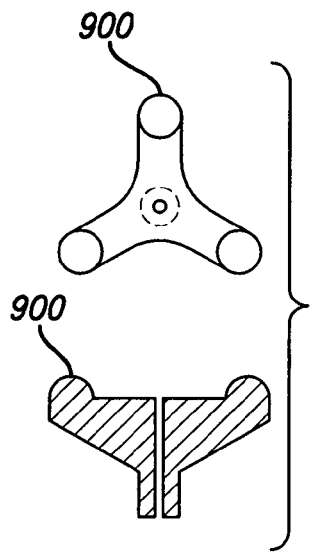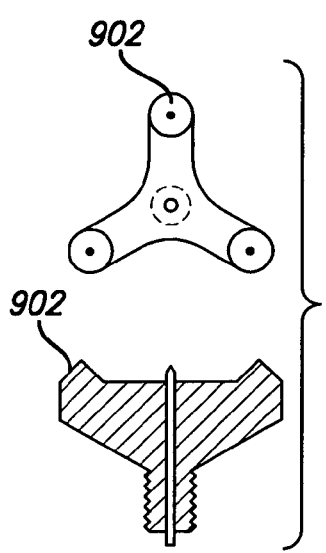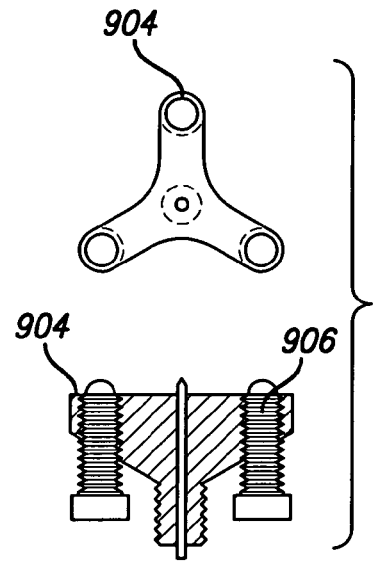
FIG. 9A    FIG. 9B    FIG. 9C
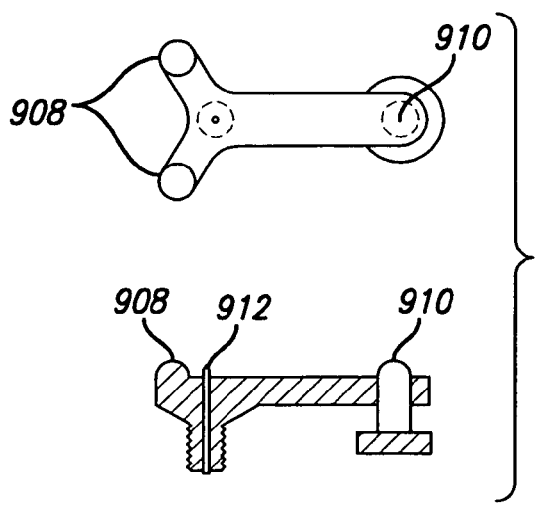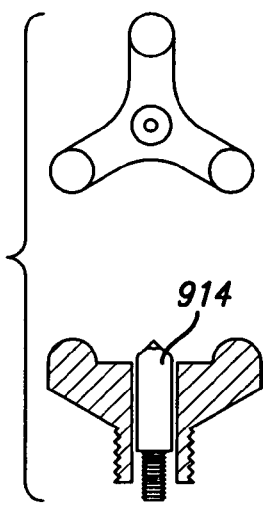
FIG. 9D    FIG. 9E

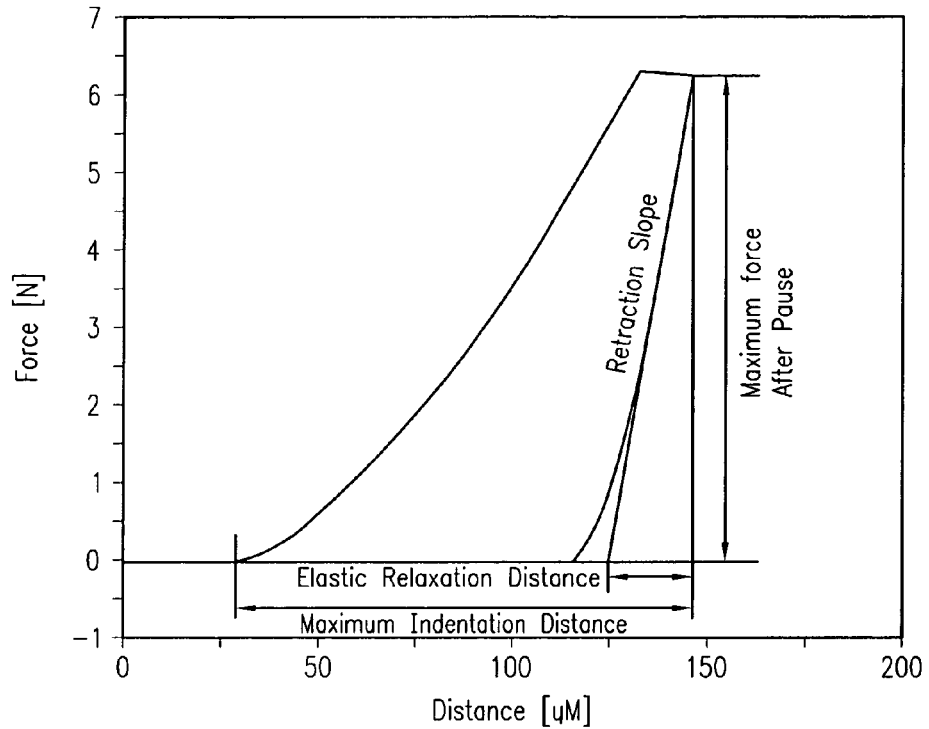

Contact Area A
Retraction Slope S
Maximum Force After Pause $_{max}$
Maximum Indentation Distance h
Contact Indentation Distance $h_c$
Hardness H
Elastic Modulus E
Poisson Ratio $\nu$
Indenter cone half-angle $\Theta$ $$h_c = h - 0.72 \frac{P_{max}}{S}$$

$$A = \pi h_c^2 \tan(\Theta) \sqrt{1+\tan(\Theta)}$$

$$H = \frac{P_{max}}{A}$$

$$E_{sample} = \frac{1 - \nu_{sample}^2}{\frac{2\sqrt{A}}{\sqrt{\pi} S} - \frac{1 - \nu_{indenter}^2}{E_{indenter}}}$$

FIG. 18
PRIOR ART

METHODS AND INSTRUMENTS FOR MATERIALS TESTING

CROSS-REFERENCE TO RELATED APPLICATIONS

This application claims the benefit of Provisional Patent Application No. 60/921,788, filed Apr. 3, 2007, which is incorporated herein in its entirety.

STATEMENT REGARDING FEDERALLY SPONSORED RESEARCH OR DEVELOPMENT

This invention was made with Government support under Grant no. RO1 GM 065354-05 from the National Institutes of Health and Grant no. NCC-1-02037 from NASA. The Government has certain rights in this invention.

FIELD OF THE INVENTION

The invention relates to an apparatus and method for materials testing.

BACKGROUND OF THE INVENTION

Indentation testing to determine the hardness of materials has a long history. Conventional indentation tests include the Brinell hardness test, the Rockwell hardness test, and the Vickers hardness test. The Brinell and Vickers tests involve indenting at a fixed load and then examining the diameter of the indentation. As shown schematically in FIG. 1A, the Rockwell test, which is the most commonly used test, involves measuring the depth of indentation from a fixed load by measuring how far a test probe 102 goes into the material under test 104. This requires a rigid frame 106. It cannot work if there is a soft layer in the mechanical path from the top of the material under test 104 down through the rigid frame 106 and back to the test probe 102 that will deform during indentation (as indicated schematically by the springs 108 in FIG. 1C) because the distance that the test probe 102 goes into the material under test 104 cannot be distinguished from the deflection of the soft layer. A real example of this problem would be attempting to measure the Rockwell hardness of a bone surface exposed during surgery. The soft tissue between the bone and the table on which the body rested would be like the springs 108 shown in FIG. 1C.

The development of very sensitive methods for measuring the depth of indentations such as capacitance sensors, optical beam deflection, laser interferometers or even very sensitive linear variable differential transducers, LVDTs, together with the development of sophisticated techniques for determining mechanical parameters from force vs. distance data only, (ref. W. C. Oliver and G. M. Pharr. Measurement of hardness and elastic modulus by instrumented indentation: Advances in understanding and refinements to methodology. J. Mater. Res. 19 (2004), 3. (review article)), has made possible a new class of indentation machines called nanoindentation testers or nanoindenters. They typically use submicrometer indentations. Nanoindentation testors also use a rigid frame 106 as shown schematically in FIG. 1A to enable accurate measurement of the distance that an indenter goes into the sample at a fixed load for macroindentation tests or variable loads for nanoindentation tests. Again, a substantial soft layer under the sample as shown in FIG. 1C would prevent accurate nanoindentation testing.

This solution to the problem of soft layers has been previously implemented, for example, in U.S. Pat. No. 1,770,045, with a durometer as shown in FIG. 2A. In this case a rigid frame is not needed because the base of the durometer 202 rests directly on the material under test 204 and indentations of the test probe 206 (sometimes called the foot) into the material are measured relative to the position of the base of the durometer 202. However, durometer indentation measurements only characterize the material with a hardness number. Attempts have been made to relate hardness measurements taken with a durometer to the elastic modulus of the material. However, no accurate, widely accepted model is available. This is in part due to the difficulties in theoretical analysis arising from the complex indenter geometry, and the inability to correct for time-dependent effects because of a lack of control of the loading rate with the durometer [Briscoe, B. J. and Sebastian, K. S. An analysis of the durometer indentation. Rubber Chemistry and Technology 66 (5): 827-836 1993)].

Other prior art portable hardness testers also exist. In particular there are many rebound testers such as the TH130 and TH150 pocket-size hardness tester from Corvib and many ultrasonic hardness testers such as the High Resolution SH-21 Portable Hardness Tester from Micro Photonics Inc. Here too, however, to the best of our knowledge there exists no portable tester that measures more material properties beyond just hardness.

One approach to indentation measurement on soft samples is to use, as a distance reference, the upper surface of the sample as is found in the instrument outlined in U.S. Pat. No. 6,142,010. In spite of this improvement, this instrument is limited in that it is solely designed for measuring hardness and relies on an external mechanical frame (as opposed to a reference probe) to maintain a rigid mechanical path between the sample and the distance measurement. The upper surface of the sample is used for a differential measurement of the indentation depth in the CSM Indentation Testers, which can measure more that just hardness. Here again, however, a rigid frame is present.

Atomic Force Microscopes (AFMs) can rest on the surface of the material under test and could, in principle at least, be used for indentation tests [C. A. J. Putman, H. G. Hansma, H. E. Gaub, and P. K. Hansma, Langmuir 8, 3014 (1992)]. An example of indentation tests on bone with the AFM is James B. Thompson et al., Nature 414, 774, 13 Dec. 2001, though this was done with a prototype AFM that was not capable of resting on the surface of the material under test.

One AFM company, Asylum Research, has also produced a nanoindenter, the MFP-3D NanoIndenter™ for Quantitative Surface Characterization. This instrument eliminates the problem of angular motions of cantilevers and goes to higher forces, up to 14 milliNewtons. It consists of a new NPS™ Nanopositioning sensor for their MFP-3D™ Stand Alone Atomic Force Microscope. The sample is held rigidly to the MFP-3D scanner through specialized sample mounts. Thus it is not designed to rest on the surface of the sample as for the present invention.

Other publications dealing with prior art systems include: U.S. Pat. No. 5,450,745; U.S. Patent Publication Nos. 2002/0170360 and 2005/0262685; "Micro Hardness Tester (MHT) for fracture toughness determination of brittle materials", No. 8, July 1998; CSM Indentation Testers, four page brochure; and "ASTM Proposed Instrumented Indentation Testing Standard", pages 1-4, October 2003.

Thus, while there have been portable hardness testing devices and devices that measure parameters other than hardness, we are aware of no prior device that combine the ability to be portable with the ability to measure a wide variety of parameters based on indentation of a probe into a sample.

BRIEF SUMMARY OF THE INVENTION

The present invention overcomes the foregoing drawbacks in providing improvements in the technology for measuring material properties of materials such as bone in a living person, teeth, the leg bones of race horses, the wing of an aircraft, the surface of a part during manufacturing or assembly and other structures that are not easily tested in conventional mechanical testers.

The invention is designed to measure more parameters than just hardness. This is important for many applications such as predicting bone fracture resistance or monitoring fatigue damage in airplane wings where measurements of hardness alone are not sufficient. Thus, compared with the devices referred to above in the BACKGROUND OF THE INVENTION section, the invention extends the capabilities of previous instruments for measuring the material properties of materials under test by making it possible to measure more material properties than just hardness with a portable instrument. Moreover, the instrument can be portable and hand held. At the heart of the invention is a measurement head that contains a reference probe that rests substantially on the surface of the material under test and provides a reference for measuring the distance that a test probe indents the material under test. The invention can, optionally, measure complete force vs. distance curves during one or multiple indentation cycles where the force is the force that the invented instrument supplies during the indentation cycle(s).

More particularly, in a departure from prior devices, we provide a device and method for characterizing a material using a test probe and constructed for insertion into the material and a reference probe aligned with the test probe in a housing. The housing is hand held or placed so that the reference probe contacts the surface of the material under pressure, applied either by hand or by the weight of the housing, causing the test probe to indent the material while maintaining the reference probe substantially under said pressure. This allows the evaluation of one or more properties of the material related to indentation of the material by the probe.

Referring again to FIGS. 1A-1D, the invention replaces the rigid frame 106 with a reference probe 110 that rests directly on the surface of the sample. Now, as will be further detailed below, the relevant mechanical path will be from the material up through the reference probe 110 and back down to the test probe 102.

The invention increases the capability of the durometer by adding a measurement head containing electronic actuators to generate forces and/or displacements as well as sensors for load and displacement that are coupled to a computerized data generation, collection and analysis system to get many parameters beyond just hardness. Compared with other instrumented indentation systems capable of measuring properties beyond hardness, our invention greatly increases the ability to test samples with complex geometries or in locations where attachment of a sample to a rigid sample holder is impossible.

The invention is also distinct from the above described AFMs in that the test probes of the invention are not mounted on cantilevers as for the AFMs. Thus there is not the problem of angular motions of cantilevers. Also, the preferred embodiments of the present invention typically go to much larger forces, several Newtons, compared to the microNewtons, nanoNewtons or below as typical of AFMs. This is an advantage for testing real materials without special surface preparation because the probed volume is large enough to be insensitive to thin surface layers of, for example, the water that covers most materials in ambient environments, and surface topography.

An additional feature of the invention is an optional wireless connection between a portable measurement head, which contains the mechanical components necessary for the measurements together with some electronics, and a base station, which contains electronics including, optionally, a computer. The base station can both supply instructions for the measurements and acquire data from the measurements.

Another additional feature of the invention is the optional ability to hand-hold the measurement head. This increases the ease and speed with which measurements can be made on complex structures such as airplane landing gear or a race horse's leg. The combination of wireless operation and a hand held measurement head is particularly useful for measurements in the field: outside a testing lab.

Still another feature enabling a compact hand-holdable instrument with the extensive capabilities of the invention is the use of opposing flexures with a linear translation stage that facilitate incorporation of a voice coil actuator.

BRIEF DESCRIPTION OF THE DRAWINGS

For a more complete understanding of the present invention, reference is now made to the following descriptions taken in conjunction with the accompanying drawing, in which:

FIGS. 8A-8D depict an alternate design for the flexures used in the embodiments of FIGS. 3 and 4. This flexure has lower stiffness than the one depicted in FIG. 6;

FIGS. 9A-9E depict various reference probes that can be used with the measurement head of this invention shown in FIG. 3;

FIG. 18 shows prior art equations [W. C. Oliver and G. M. Pharr. Measurement of hardness and elastic modulus by instrumented indentation: Advances in understanding and refinements to methodology. J. Mater. Res. 19 (2004), 3.] for calculating Hardness and Elastic Modulus;

DETAILED DESCRIPTION OF THE INVENTION

The essential feature of the invention is a probe that is inserted into a material under test a distance that is measured relative to a reference probe, which rests substantially on the surface of the material under test. In a preferred embodiment, the probe consists of a steel shaft tipped with a sharpened diamond. It slips inside a three footed reference probe with feet on a circle of diameter approximately 1.5 inches. A typical penetration depth is 0.05 mm.

The method is particularly suited to evaluating one or more properties of a living human bone of a subject, the test probe being inserted through the periosteum and/or soft tissue on the bone so that the test probe contacts the subject's bone. Such an evaluation is described in our previous work on developing a bone diagnostic Instrument, filed in U.S. patent application Ser. No. 11/417,494 filed May 3, 2006 titled Methods and Instruments for Assessing Bone Fracture Risk, the disclosure of which is incorporated herein by reference.

In one class of embodiments, the probe and reference probe are connected to a measurement head. This measurement head can be connected to a base station either with wires or with a wireless connection. This measurement head can be held on the material under test with a stand or it can be hand held or it can be hand held with the help of an optional support. This optional support can, for example, serve to hold the measurement head at a fixed angle relative to the surface of the material under test during the test process.

The test process consists of one or more indentation cycles during which the force applied to the probe and the distance that the probe is inserted into the material under test are measured. These measurements can be analyzed to give material parameters such as Elastic Modulus, Hardness, Adhesion (that is the maximum force needed to pull the probe out of the material), Elastic Energy Dissipation, Plastic Energy Dissipation, Total Energy Dissipation, Maximum distance of insertion, and Maximum Force during the cycle. All of these parameters can be measured as a function of time through a series of cycles. For example, we sometimes measure bone parameters over a series of 80 cycles at 3.5 Hz. Additional useful parameters are the ratios of the final to initial values of the individual parameters: for example, the ratio of the Plastic Energy Dissipation on the final cycle to the Plastic Energy Dissipation on the first cycle. It has turned out that the ratio of the final value of Hardness to the initial value of the Hardness on bone is correlated with resistance to bone fracture.

Figure 1A:
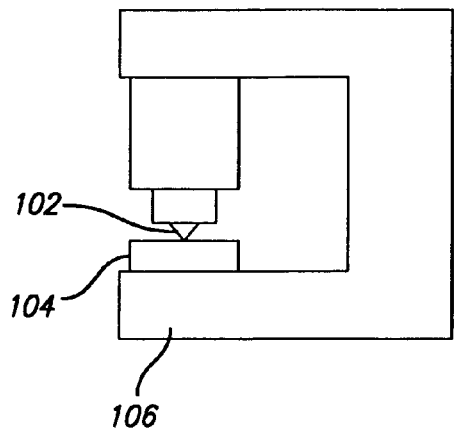
FIGS. 1A-1D are schematic drawings illustrating the advances in the present invention over the prior art instruments that rely on a rigid frame for measuring the depth of indentation.
Figure 1B:
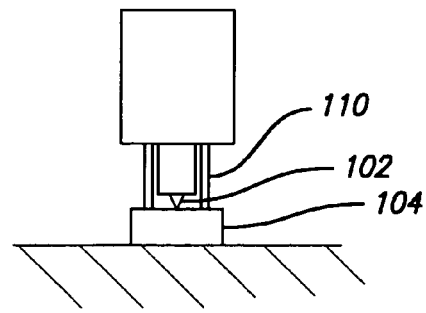
Figure 1C:
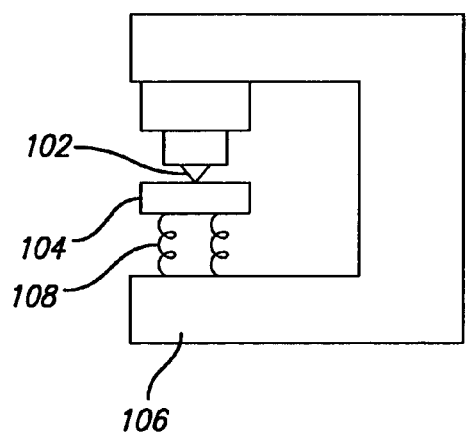
Figure 1D:
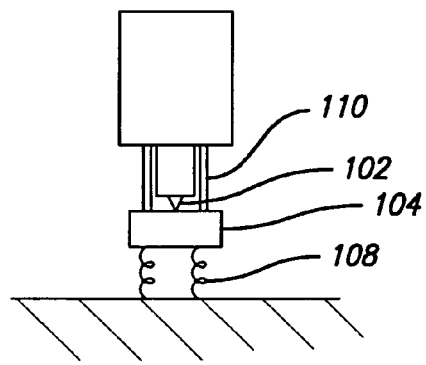
Figure 2A:
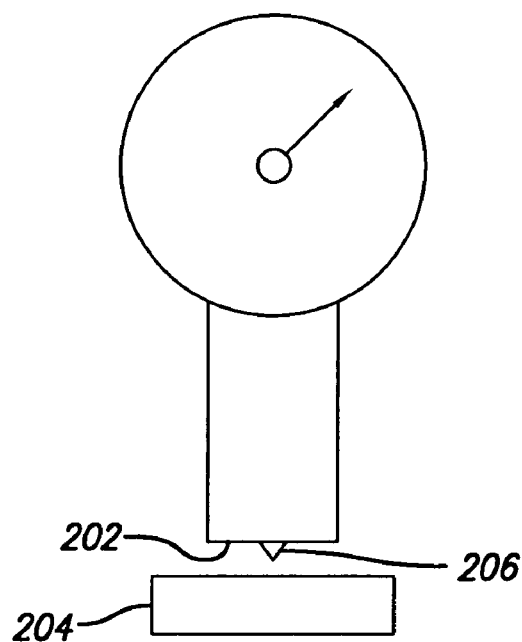
FIGS. 2A and 2B are schematic drawings illustrating the advances in the present invention over the prior art instruments called durometers.
Figure 2B:
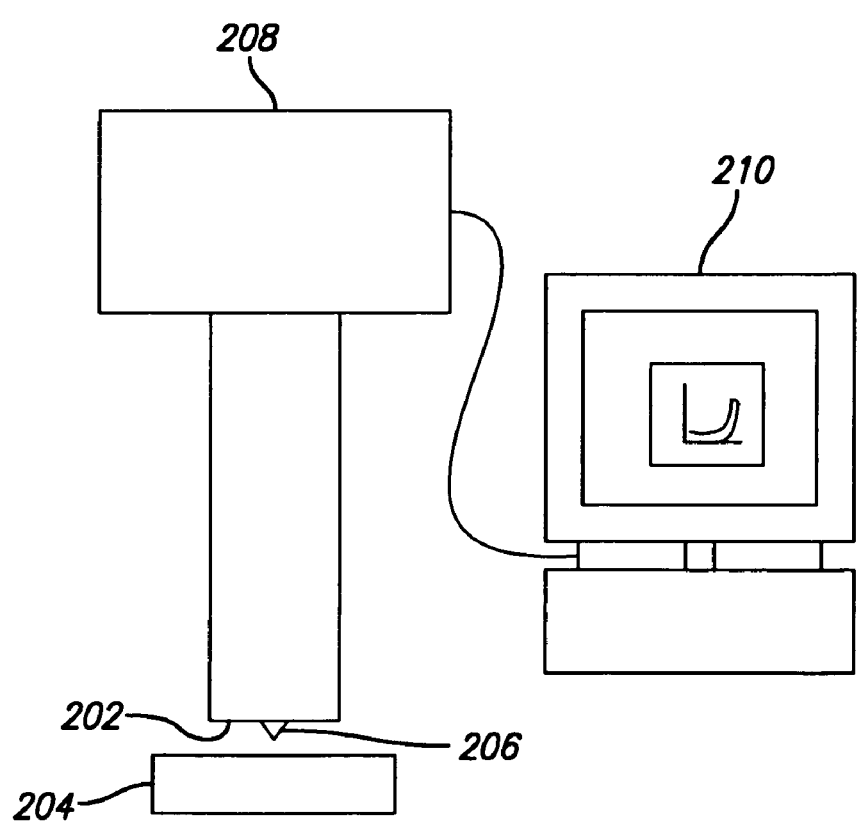
Figure 3:
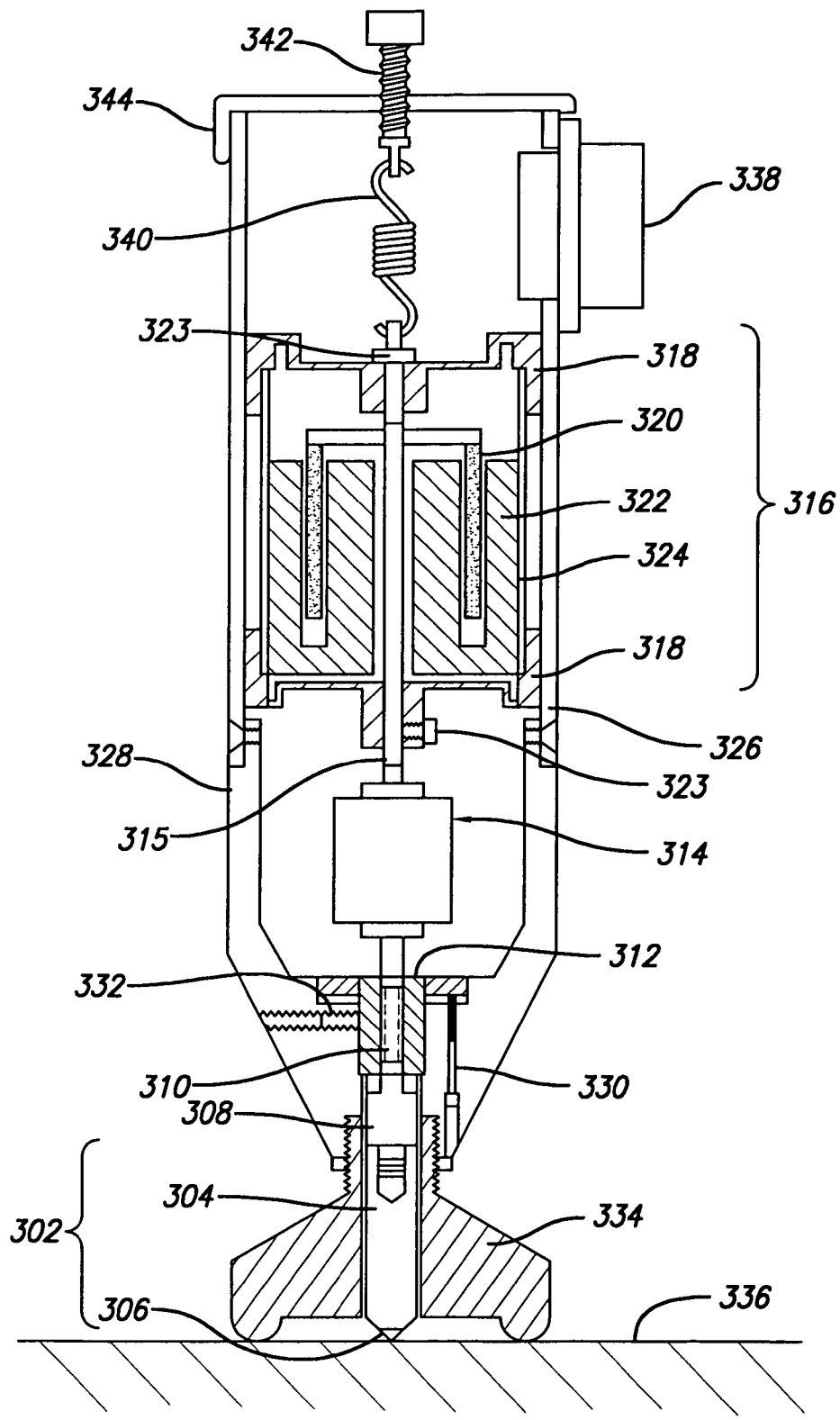
FIG. 3 is a cross-sectional view of the measurement head of this invention in accordance with one embodiment.

FIG. 3 is a detailed drawing of the measurement head of a currently preferred embodiment of our invention. A test probe 302 consisting of a shaft 304 and a sharp tip (often a diamond) 306 is attached to a shaft 308 that connects to the core 310 of an LVDT 312 (for example Measurement Specialties MHR 025). This in turn connects to a load cell 314 (for example Futek LSB 200) and then, with a shaft 315, to a force generator 316 consisting of two flexures of novel design 318, (which will be described in more detail in FIGS. 6, 7 and 8) together with a voice coil actuator (a modified version of BEI Kimco Magnetics LA16-27-000A) which consists of a moving coil 320 in a magnetic field assembly 322. The flexures 318 are attached with screws 323. This force generator 316 is anchored in an inner shell 324 that is capped by the flexures 318. The force generator 316 is held in an outer shell 326. The outer shell is connected to a nose piece 328, which supports the LVDT body 312. The position of the LVDT body 312 can be adjusted to zero or otherwise adjust the signal from the LVDT 310, 312 with a fine screw 330 and is locked into place with set screws 332. The nose piece 328 also rigidly supports a reference probe 334 that rests on the surface of the sample under test 336. The measurement head can be hand held during the test, which has the advantage that it can be forced against the sample under test with greater force than its own weight. In general the largest force that can be applied by the force generator 316 to the sample under test 336 must be less than the force with which the measurement head is pressed against the surface. Otherwise the measurement head will lift off the sample under test 336. This greater force with hand held operation allows greater maximum force during the measurement of force vs. distance curves. Hand held operation also allows measurements on surfaces that are not substantially horizontal and measured from above. Alternately, elastic elements such as springs or rubber tubes or bungee cords can used to hold the measurement head against the sample under test.

The electrical signals to actuate the force generator 316 as well as the force signal from the load cell 314 and the distance signal from the LVDT 310, 312 pass through an electrical connector 338 (AMP 28 pin connector). An optional adjustment of the initial position of the test probe 302 relative to the reference probe 334 can be made with an optional spring 340 that is pulled with an optional screw 342 that is threaded through a cap 344. The bandwidth of both the LVDT 310,312 and the load cell 314 and both their amplifiers and the data acquisition system is 1 kHz or above. Thus the instrument can be operated to obtain complete force vs. distance curves in cycle times as fast as 0.1 second. For maximum resolution, cycle times as fast as 1 second are more typical. For maximum speed, cycle times as fast as 0.01 second have been used, but the force vs. distance curve is not accurately captured. Fast cycle times can, however, be used to test for damage during cyclic loading with, optionally, slower, more accurate curves taken before and after the fast cyclic loading.

Figure 4:
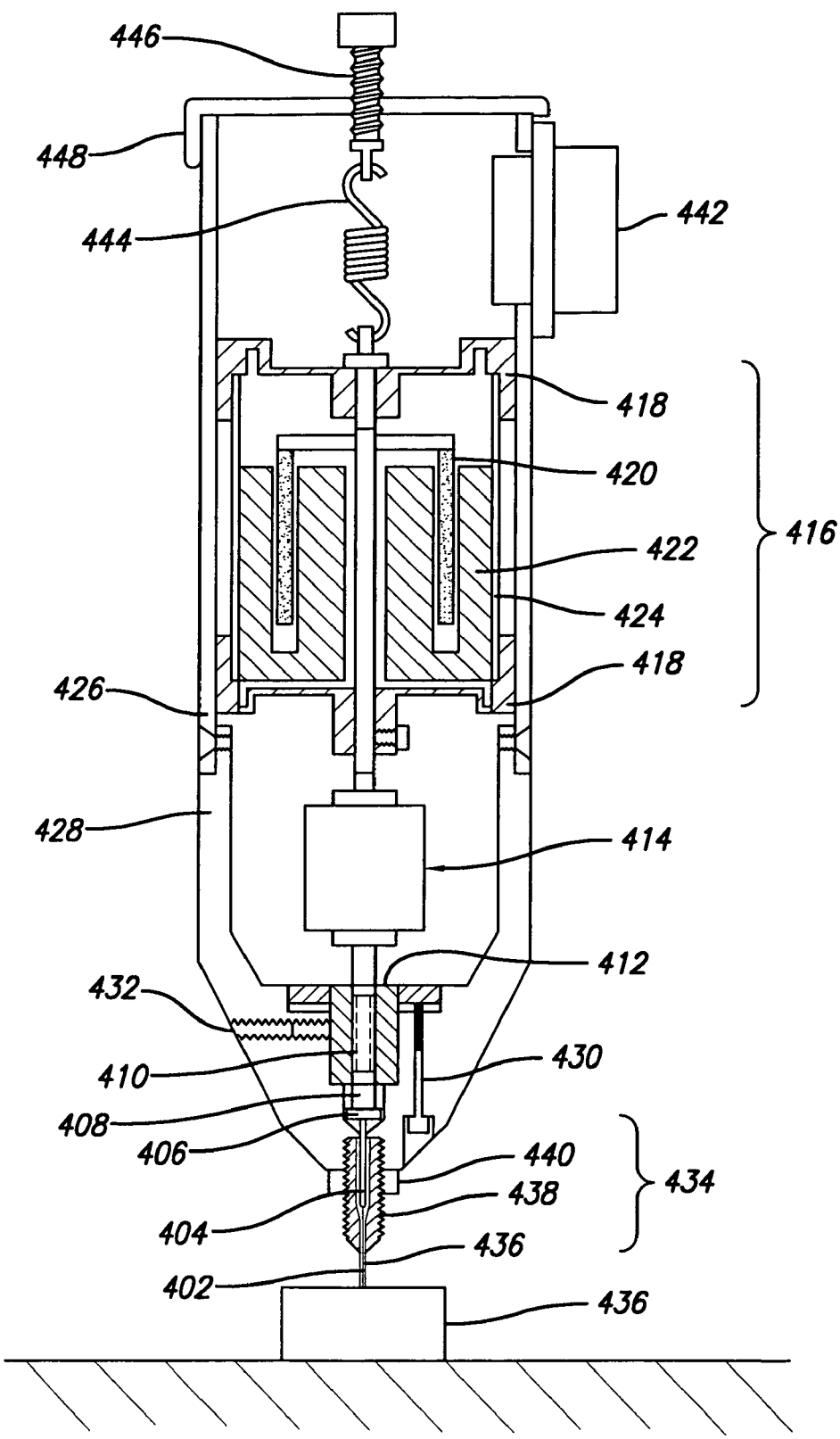
FIG. 4 is a cross-sectional view of the measurement head of this invention in accordance with one embodiment.

FIG. 4 is a detailed drawing of another version of the measurement head of a currently preferred embodiment of our invention. This version is designed to be used as Bone Diagnostic Instrument (Methods and Instruments for Assessing Bone Fracture Risk U.S. patent application Ser. No. 11,417,494) for which soft tissue overlying the bone must be penetrated in order to measure the properties of the underlying bone. In this version the test probe 402 is a sharpened steel rod of diameter 0.015" held in a mounting pin 404 which attaches magnetically to a permanent magnet 406 that is attached to a shaft 408 that connects to the core 410 of an LVDT 412 (for example Measurement Specialties MHR 025). This in turn connects to a load cell 414 (for example the Futek LSB 200 or the Sensotec Model 34 precision miniature load cell) and then to a force generator 416 consisting of two flexures of novel design 418, which will be described in more detail in FIGS. 6, 7 and 8) together with a voice coil actuator (a modified version of BEI Kimco Magnetics LA16-27-000A) which consists of a moving coil 420 in a magnetic field assembly 422. This force generator 416 is anchored in an inner shell 424 that is capped by the flexures 418. The force generator 416 is held in an outer shell 426. The outer shell is connected to a nose piece 428, which supports the LVDT body 412. The position of the LVDT body 412 can be adjusted to zero or otherwise adjust the signal from the LVDT 410, 412 with a fine screw 430 and is locked into place with set screws 432. The nose piece 428 also rigidly supports a reference probe 434 that rests on the surface of the sample under test 336. In this version the reference probe 434 consists of small diameter stainless steel tubing 436 held in a brass body 438 that is threaded into the nose piece 428 and held rigidly in position with a knurled locking nut 440

The electrical signals to actuate the force generator 416 as well as the force signal from the load cell 414 and the distance signal from the LVDT 410, 412 pass through an electrical connector 442 (AMP 28 pin connector). An optional adjustment of the initial position of the test probe 402 relative to the reference probe 434 can be made with an optional spring 444 that is pulled with an optional screw 446 that is threaded through a cap 448.

Figure 5A:
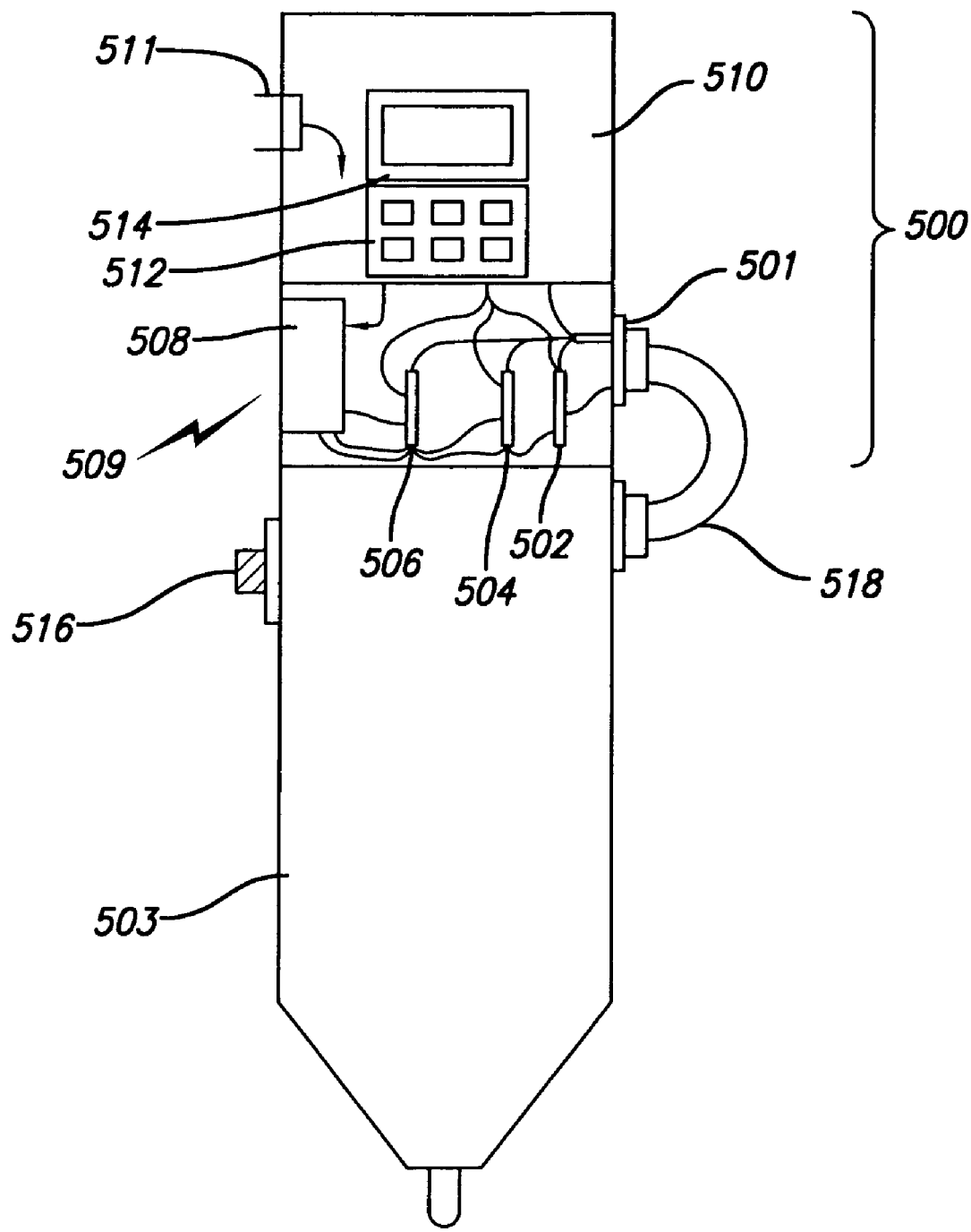
FIGS. 5A and 5B depict a portable embodiment of the instrument with wireless connection between a portable measurement head of this invention, which contains the mechanical components necessary for the measurements together with some electronics, and a base station, which contains electronics including, optionally, a computer.
Figure 5B:
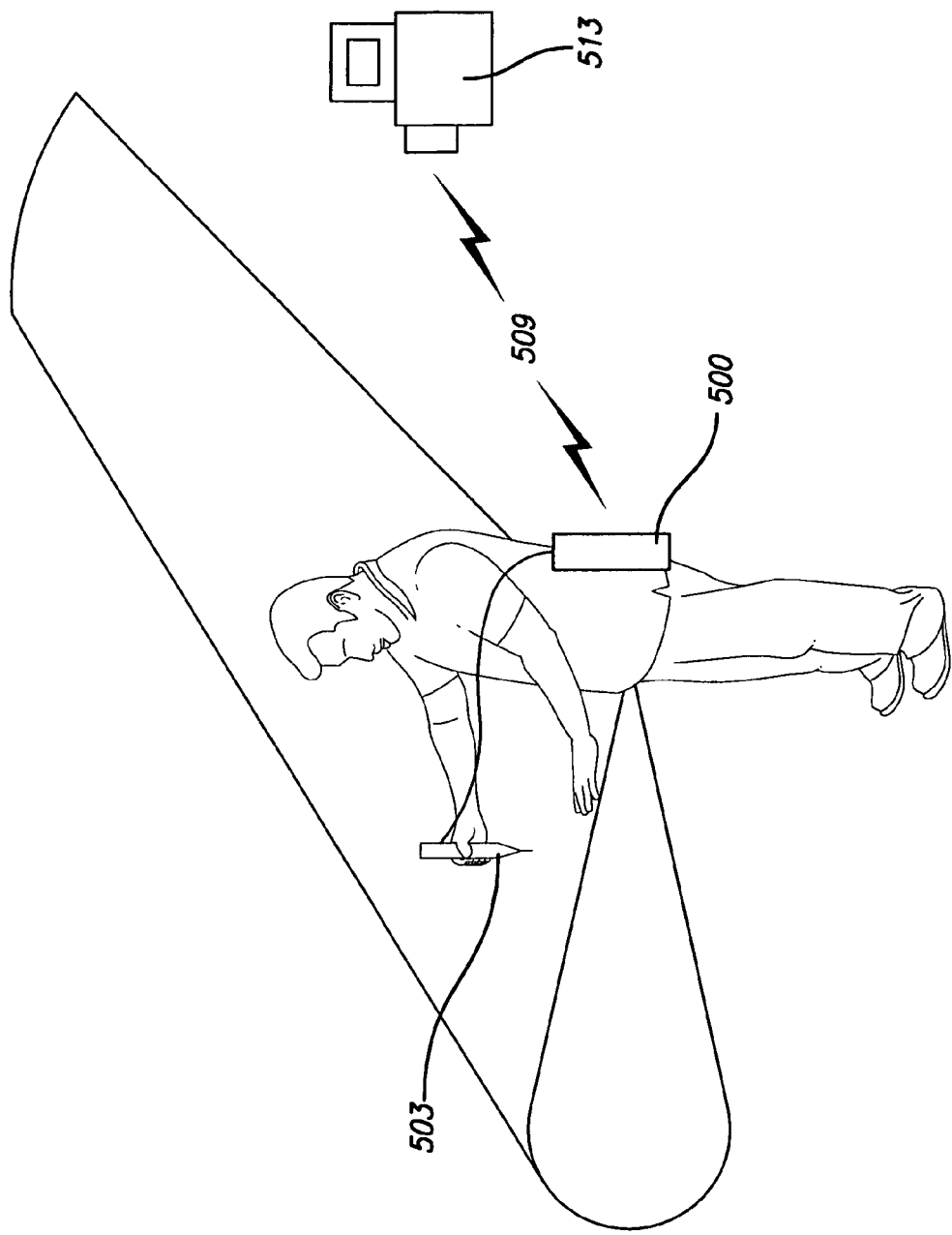

FIGS. 5A and 5B shows how the currently preferred embodiments of our invention can be made wireless. The measurement head 503 (shown in more detail in FIGS. 3 and 4) is combined with a wireless adapter/power pack module 500 for the instrument. This module 500 has many functions including: supplying power for the instrument, amplifying and conditioning the signals from the transducers, the transmission of data, the reception of input signals, and the amplification of input signals.

The transmission of the data starts at the connector 501, where the interface with the instrument is located. The signal for the distance sensor (from the instrument) is sent through the connector 501 to the PC board with distance sensor amplifier and signal conditioner 504. Here the signal is amplified and then sent to the wireless module 508. The data is then sent to the partner computer(s) 513 (FIG. 5B) with electromagnetic radiation 509. The signal from the load cell (from the instrument) goes through the connector 501 to the PC board with load cell amplifier and signal conditioner 502. Here the signal is amplified and conditioned and then sent to the wireless module 508 where it is transmitted to the partner computer(s) 513 with electromagnetic radiation 509.

Input signals are received via electromagnetic radiation 509 by the wireless module 508. The signals are then transmitted to and amplified by the PC board with amplifier 506 that drives the force generator 416. The amplified signal is then sent to the force generator 416 in the instrument via the connector 501.

The whole system, including the instrument, may be powered from the rechargeable battery 510. The battery itself has an energy port 511 where external power can be introduced into the system to either recharge the battery or power the wireless module externally. The battery 510 may also be wired such that it is easily removable or replaceable. Batteries such as found in small hand tools such as cordless drills are suitable. For the force generator 416 in the currently preferred embodiment, we typically use average currents of less than 1A at voltages of a few Volts for times of order 20s thus requiring of order 0.0056 Ah per test. This can easily be supplied by the type of NiMH rechargeable batteries used in cordless drills, which can supply 3 Ah, enough for over 500 tests.

The wireless adapter/power pack module 500 can (optionally) also contain a keypad 512 to set test parameters and access selected test data and analysis on a display screen 514. For wireless use, the switch 516 can be added to the measurement head 503 (shown in more detail in FIGS. 3 and 4) to trigger test cycles conveniently.

The measurement head 503 is connected to the wireless adapter/power pack module 500 with cable 518. As shown in FIG. 5A, the cable can be external, joining the measurement head 503 to the wireless adapter/power pack module 500 that is mounted on top of the measurement head. This permits the removal of the wireless adapter/power pack module 500 if it is desired to have the measurement head connected directly to control electronics and a computer. If the unit is designed only for wireless use, the cable can, of course, be internal. Alternately the wireless adapter/power pack module 500 can be separate from the measurement head 503 as shown in FIG. 5B. This has the advantage of making the hand held part lighter and the wireless adapter/power pack module 500 more capable in terms of battery capacity, data processing and data storage.

Figure 6A:
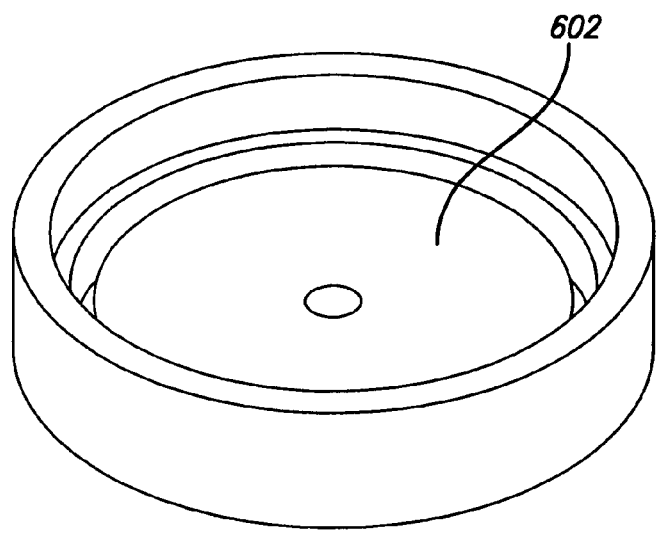
FIGS. 6A-6C depict the flexures used in the embodiments of FIGS. 3 and 4.
Figures 6B, 6C:
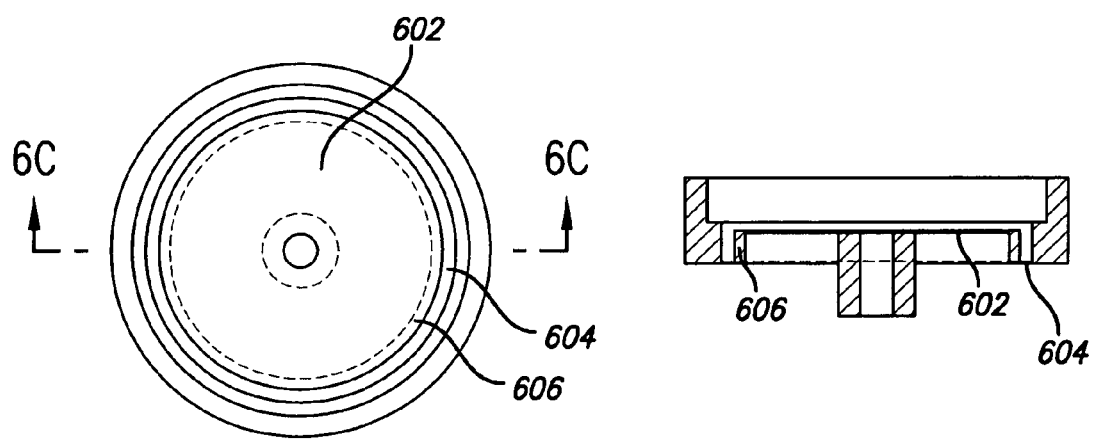
Figure 7:
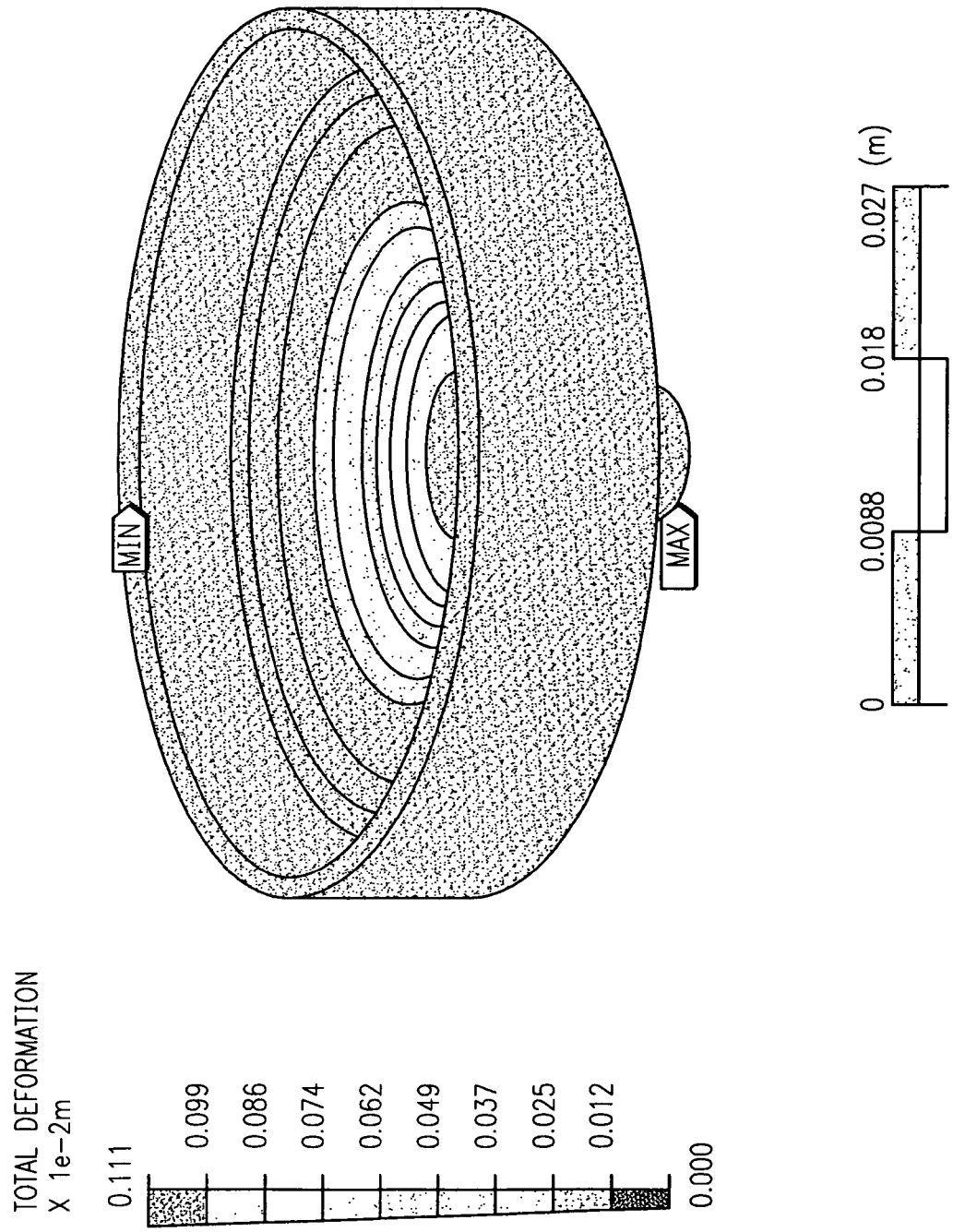
FIG. 7 depicts the finite element analysis of the flexure shown in FIG. 6.

FIGS. 6A-6C show the circular flexures used in the currently preferred embodiment of the invention. The flexures are included to guide the motion of the force generator (for example 416, FIG. 4) and ensure that there is no substantial off-axis motion. The flexures design consists of a large, horizontal, thin inner membrane 602 connected to a outer, thin, horizontal membrane 604 through a vertical ring 606. The design of the flexures was improved through the use of finite element analysis. FIG. 7 shows the results of simulating the deformation of one of the flexures under an axial load.

The softness of the circular flexure may be increased by cutting out radial sections 802 of the flexure, as shown in FIGS. 8A-8C. Further softening could be achieved by cutting away more of the circular flexure, for example, leaving only thin radial strips like spokes on a wheel.

FIGS. 9A-9E show various reference probes that can be used in place of the reference probe 334 shown in FIG. 3. 9A has three rounded feet 900 to minimize marring of the material under test. 9B has three pointed feet 902 to minimize lateral slipping. 9C has three adjustable feet 904 that contain permanent magnets 906 to minimize slipping and marring of magnetic surfaces such as steel. These magnets 906 could also be electromagnets or mechanically switchable magnets as used in magnetic bases (see, for example, 1228 in FIG. 12). 9D shows one of many possible variants of fixed 908 and adjustable feet 910. The motion of the adjustable foot 910 is demagnified at the location of the test probe 912 to give more precise positioning. 9E shows a reference probe that is suitable for use with a standard diamond indenter 914. As an example, a Rockwell Diamond Indenter with a Versitron shank 914 is shown, but, of course many others could be used with a suitably designed reference probe.

Figure 10:
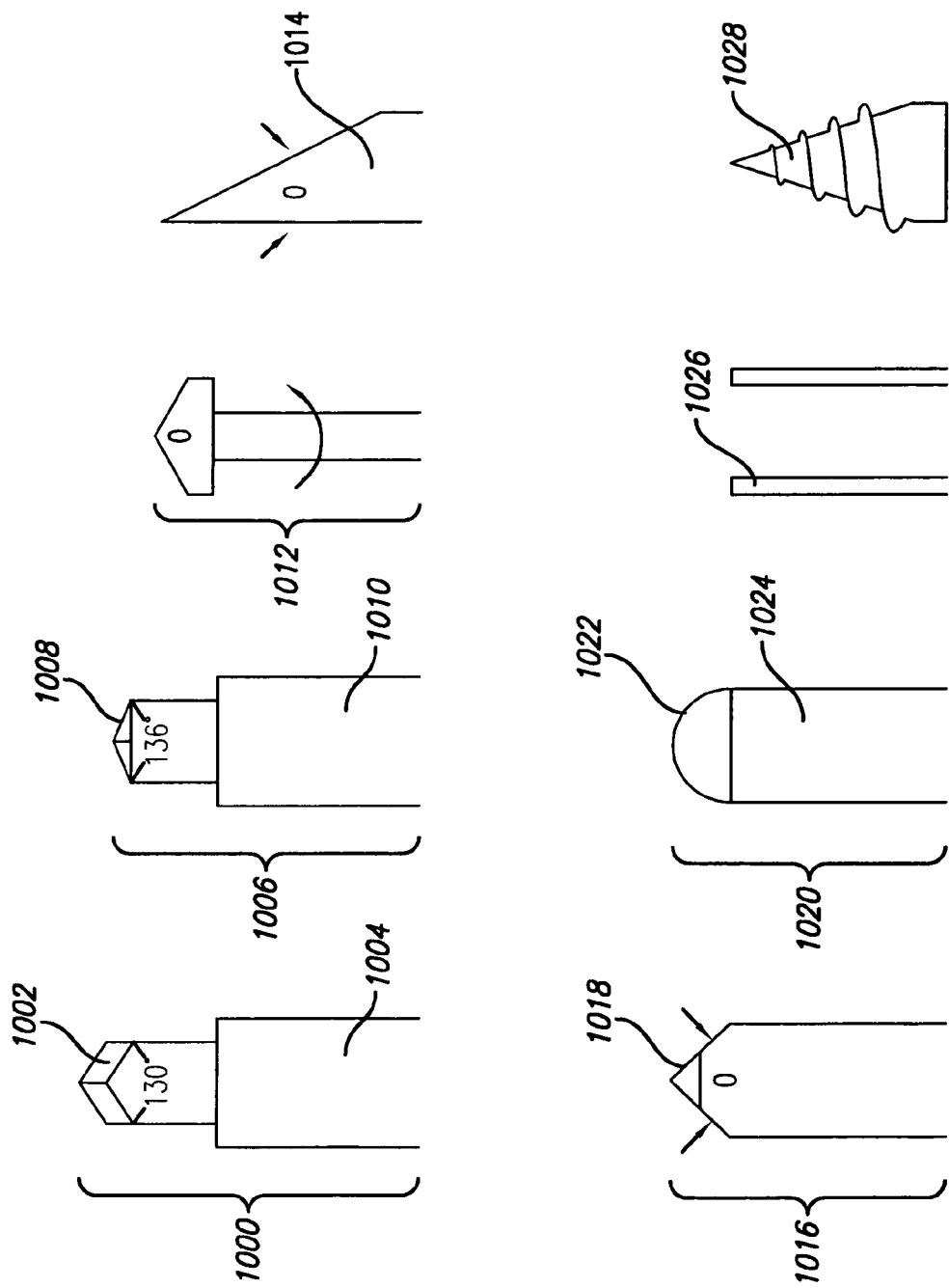
FIG. 10 depicts various test probes for the invention.

FIG. 10 shows different possibilities for the tips of test probes. Test probe 1000 is patterned on the diamond indenter used in Knoop hardness testing. It has a pyramid-shaped diamond 1002 with apical angles of 130° and about 170°, mounted on a tungsten carbide shank 1004. Test probe 1006, has a diamond 1008 in the shape of a square-based pyramid whose opposite sides meet at the apex at an angle of 136° as used in Vickers hardness testing of metals and ceramics, mounted on a ceramic shaft 1010. Test probe 1012 is a disk that can be rotated for measuring friction, $\phi=0$, or viscosity of tissue near a bone surface, at $\phi=0$ or $\emptyset>0$ as in conventional viscosity measurements. Test probe 1014 is wedge shaped and is used for assessing the fracture resistance of materials. Test probe 1016, designed for testing the material properties of bone and teeth, has a cone at its end. In a preferred embodiment $\theta=90$ and the test probe is tool steel. In other embodiments the test probe can have angles $\theta=70$ and 50 and can have a tip 1018 of a different material, such as diamond. Test probe 1020 is patterned after the indenters used in some Rockwell and Brinell hardness testing, and has a half sphere of tungsten carbide 1022 bonded to a steel shank 1024. Test probe 1026 is a tube that can be rotated for measuring friction on the surface of a material. Test probe 1028 is a screw that can test bone by measuring the torque necessary to screw it into the bone. These are only intended as representative examples. Many other geometries and test probe materials could be used.

Figure 11:
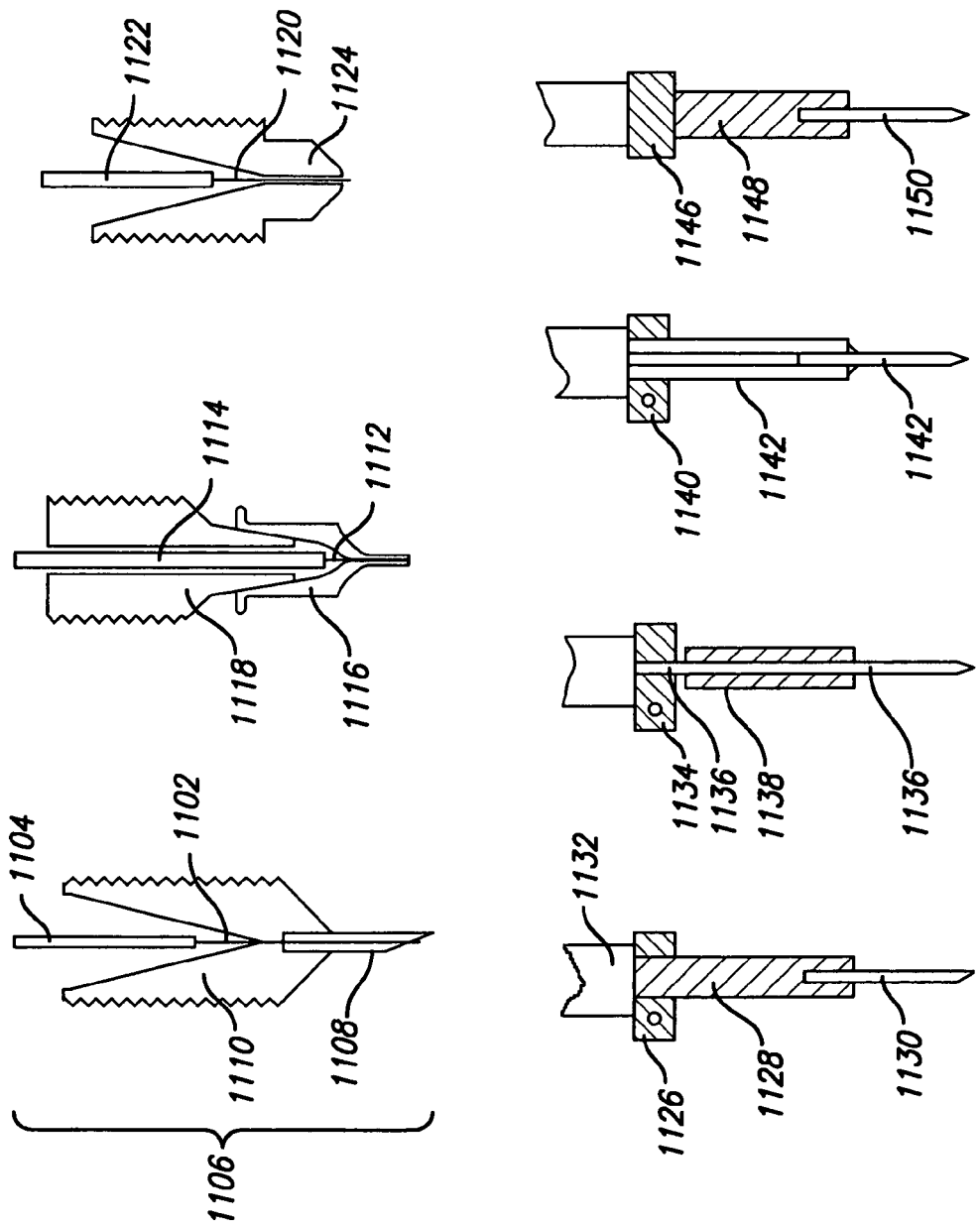
FIG. 11 depicts probe assemblies, which are combinations of test probes with reference probes, that can be used with the measurement heads of this invention show in FIGS. 4, 13, 14 and 15, showing also various ways to attach a test probe to the shaft of the measurement head of this invention and various ways to inhibit buckling of the test probe.

FIG. 11 shows details of three probe assemblies (test probes in reference probes) in the top row. In the first example, the test probe 1102 is held in a mounting pin 1104 that is a 1/16" diameter steel rod with a hole in the end into which the test probe is glued or soldered. The reference probe 1106 is composed of sharpened, small diameter tubing 1108 joined to a threaded body 1110. In the second example, the test probe 1112 is shorter, but, when mounted on a longer mounting pin 1114, gives the same overall length of mounted test probe as the previous example. In this case the reference probe is a hypodermic syringe needle 1116 that is removably mounted in a threaded Luer adaptor 1118. In the third example, the test probe 1120 is mounted in a mounting pin 1122. Here the reference probe 1124 has no tubing projecting from the end, but is suitable for use when the material under test is not covered with a layer that must be penetrated (as in the case of skin covering bone).

FIG. 11 also shows, in the bottom row, some details of an alternate to the magnet shown as 406 in FIG. 4 for holding mounted test probes. The collet 1126 holds the mounting pin 1128 for the test probe 1130. This collet 1126 is attached to a shaft 1132, shown as 408 in FIG. 4. The collet 1134 holds the test probe 1136 directly. The tube 1138, which can optionally be attached to the test probe 1136, functions to minimize buckling of the test probe 1136. The collet 1140 holds a tube 1142 in which the test probe 1144 is mounted.

Finally, the magnet 1146 holds the mount 1148 for the test probe 1150. This test probe and all the test probes in FIG. 11 can have many tip shapes, as shown in FIG. 10.

Figure 12:
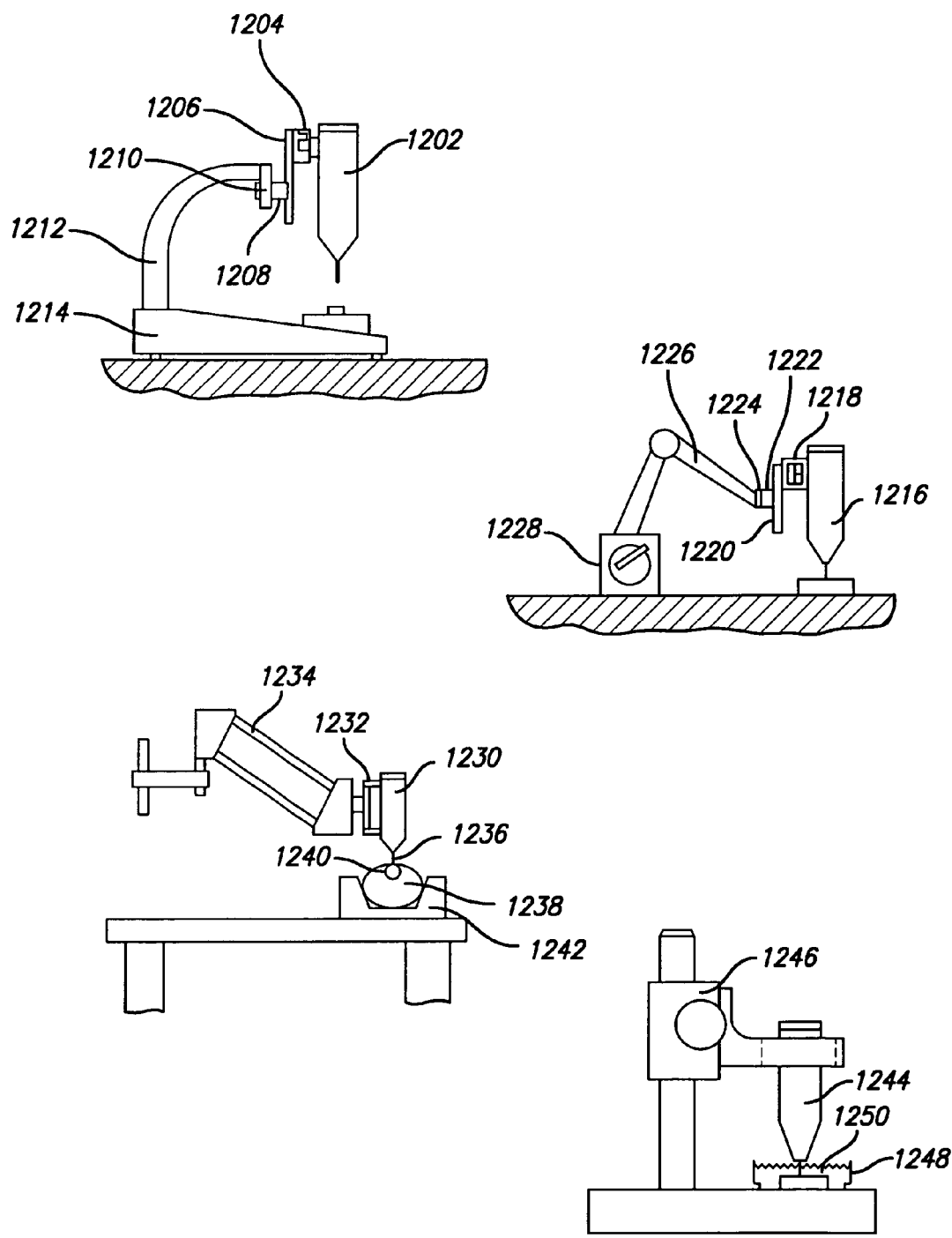
FIG. 12 depicts various support stands for the measurement head used in the invention.

FIG. 12 shows various support stands for the instrument. The instrument can be hand held, resting on the three feet of the reference probe 334 that rest on the surface of the sample under test 336 shown in FIG. 3. More reference probes for hand held use were shown in FIGS. 9A-9E. For some applications, however, it is useful to supplement or eliminate the hand holding the instrument. The goal is to stabilize the instrument more than is possible when just hand held. As some examples, the measurement head 1202 is attached with a removable mount 1204 (for example, a ¼-20 screw mount such as used for cameras) to a rail 1206 which is, in turn held in a guide block 1208 (for example, the Miniature Corrosion-Resistant Versa-Mount Guide Blocks and Rails form Mc Master Carr can be used) which is, in turn, attached with a removable mount 1210 (for example, a ¼-20 screw mount such as used for cameras can be used here also) to a support arm 1212 attached to a base 1214. This support stand allows the measurement head 1202 to move freely up and down while being constrained laterally and held vertically.

The measurement head 1216 is also mounted via a removable mount 1218 to a rail 1220 which is, in turn held in a guide block 1222 (for example, the Miniature Corrosion-Resistant Versa-Mount Guide Blocks and Rails from Mc Master Carr can be used) which is, in turn, attached with a removable mount 1224 (for example, a ¼-20 screw mount such as used for cameras can be used here also) to an adjustable arm 1226 attached to a magnetic base 1228.

The measurement head 1230 is permanently mounted by attachments at each end to a rail 1232, which is, in turn, mounted to an articulating arm system 1234 (such as the FlexArm available from Midwest Specialties Inc.). The probe assembly 1236 is shown schematically penetrating soft tissue of a leg 1238 to reach the tibia 1240. The leg is held in a modified V block 1242 to stabilize it during the measurements.

The measurement head 1244 is held in a microscope stand 1246. The material under test is in a fluid cell 1248 that is filled with fluid 1250. One of the advantages of all the embodiments shown is that it is easy to work with samples under aqueous buffers to, for example, simulate physiological conditions. It is also easy to put in a heating stage or hot plate under the fluid cell 1248 or under a material under test that is not in a fluid cell because there is no rigid frame that limits the space below the measurement head. Though FIG. 12 shows a particular microscope stand 1246, a wide variety of microscope stands are available for mounting stereo microscopes including ones for operating rooms that roll on the floor and allow the surgeon to see parts of a patient's body on the operating table. This type of rolling microscope stand could hold the measurement head 1244 for testing the bone or teeth of a patient on a table. The core assemble is mounted in a disk of the correct diameter for the particular microscope stand (typically about 3" in diameter). This mounting in the disk can be rigid (as shown) or via a rail and guide block system as shown in the other support stands. Conversely the other support stands can be used without a rail and guide block system. The advantage of the rail and guide block system is that the force of the probe assembly on the material under test is constant: the weight of the moving parts (for example the measurement head 1202, the removable mount 1204 and the rail 1206).

Figure 13:
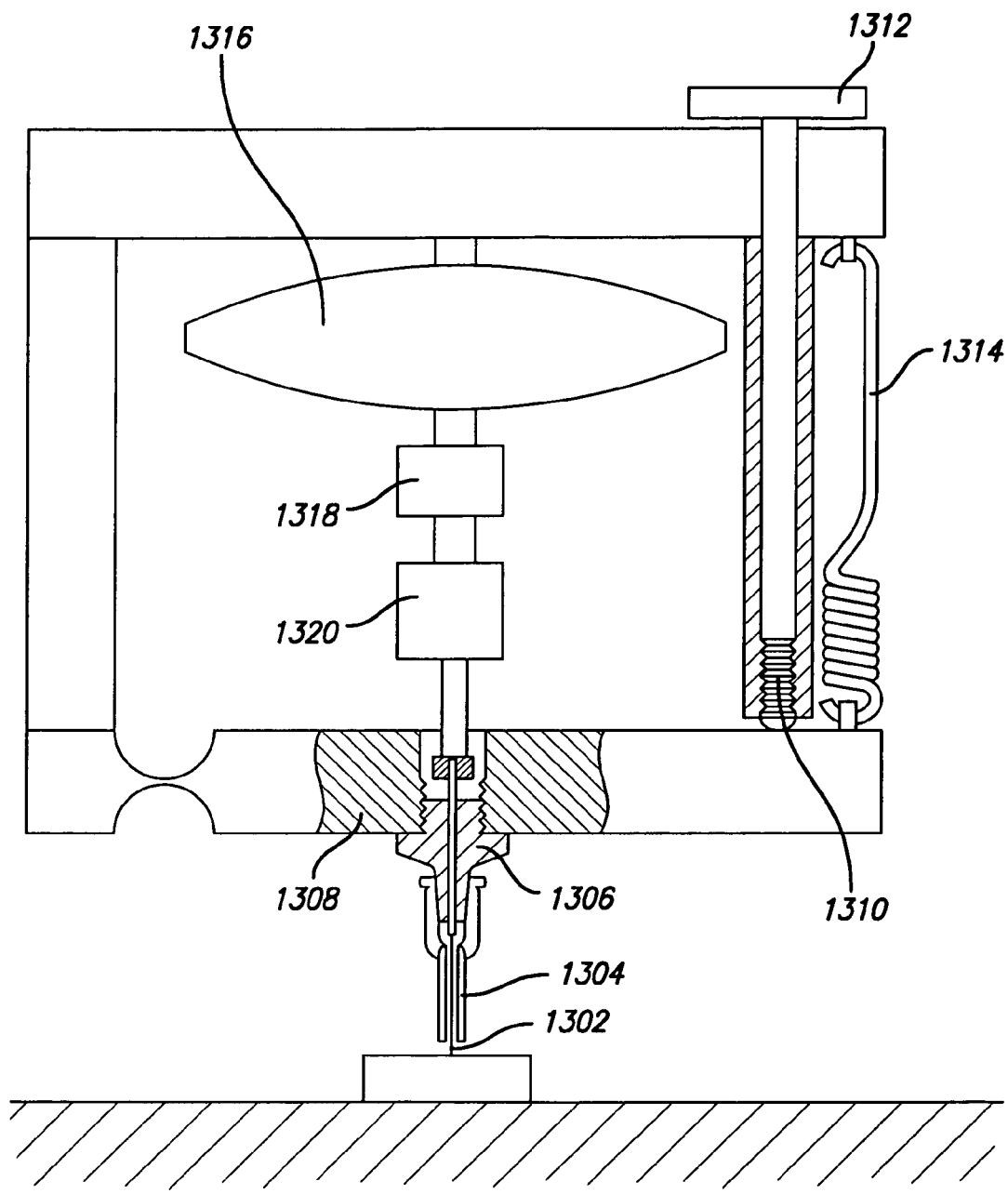
FIG. 13 is a view of the measurement head of this invention in accordance with one embodiment that contains mechanisms for both a coarse and fine adjustment of the relative position of a test probe and a reference probe.

FIG. 13 shows a previous embodiment of this invention. The position of the test probe 1302 relative to the reference probe 1304 can be coarsely adjusted by screwing the threaded Luer adaptor 1306 into or out of the frame arm 1308. Fine adjustment comes from turning the screw 1310 with the knob 1312. The frame arm 1308 is held against the tip of the screw 1310 by a spring 1314. In this embodiment the force and motion are generated by a transducer 1316 (Clark Tactile Sound Transducer, U.S. Pat. No. 5,473,700) that consists of two dome shaped disks that are joined at their edges. One supports a voice coil and the other supports a magnet structure. This figure illustrates that the force generator of this invention is not restricted to just the type of voice coil system shown in the other figures. Other alternatives for a force generator have been shown in FIG. 13 of Methods and Instruments for Assessing Bone Fracture Risk U.S. patent application Ser. No. 11,417,494). This embodiment used a load cell 1318 and an optical position detector 1320.

Figure 14A:
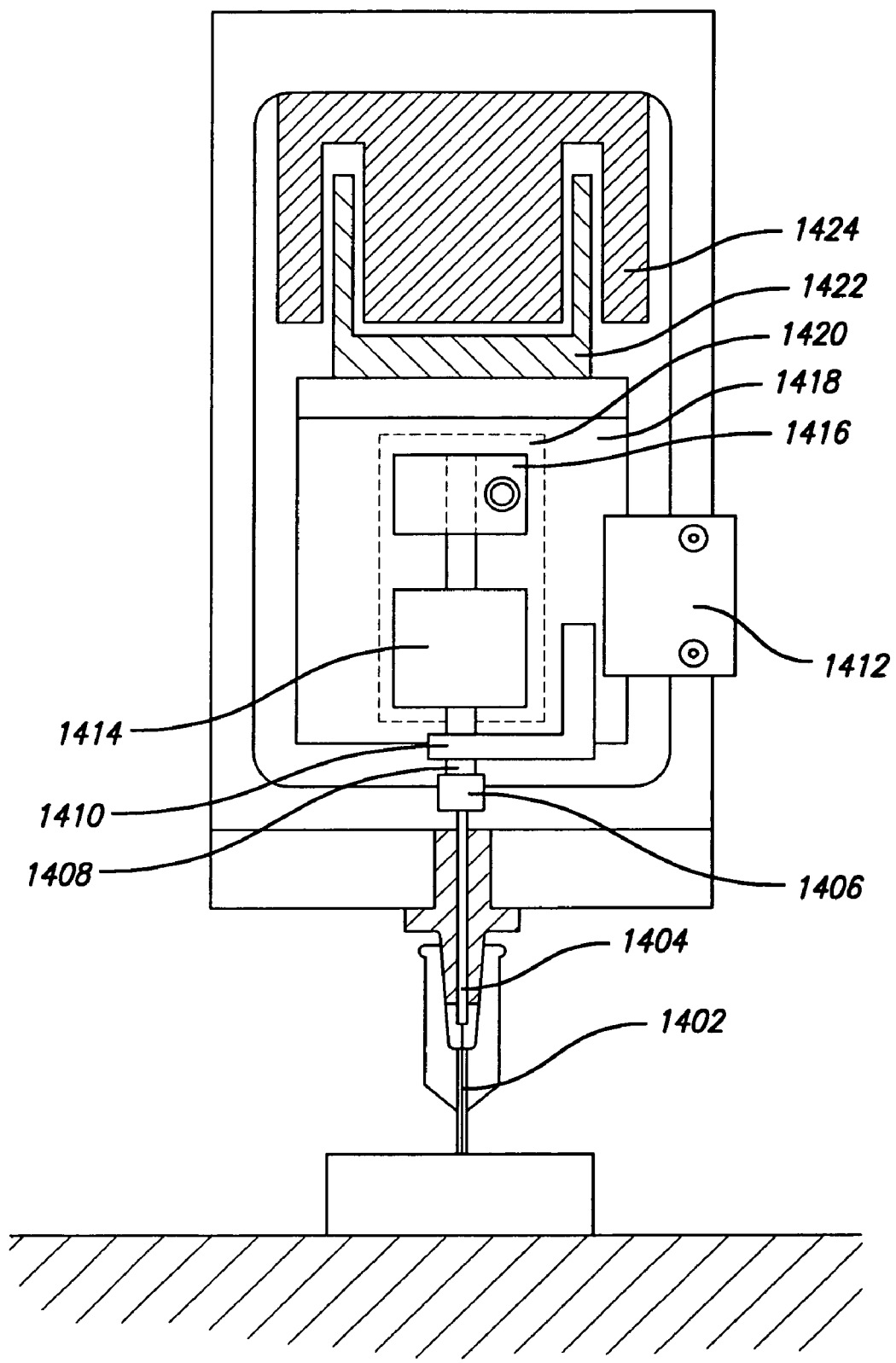
FIGS. 14A and 14B are views of the measurement head of this invention in accordance with two embodiments that use a linear stage rather than flexures.
Figure 14B:
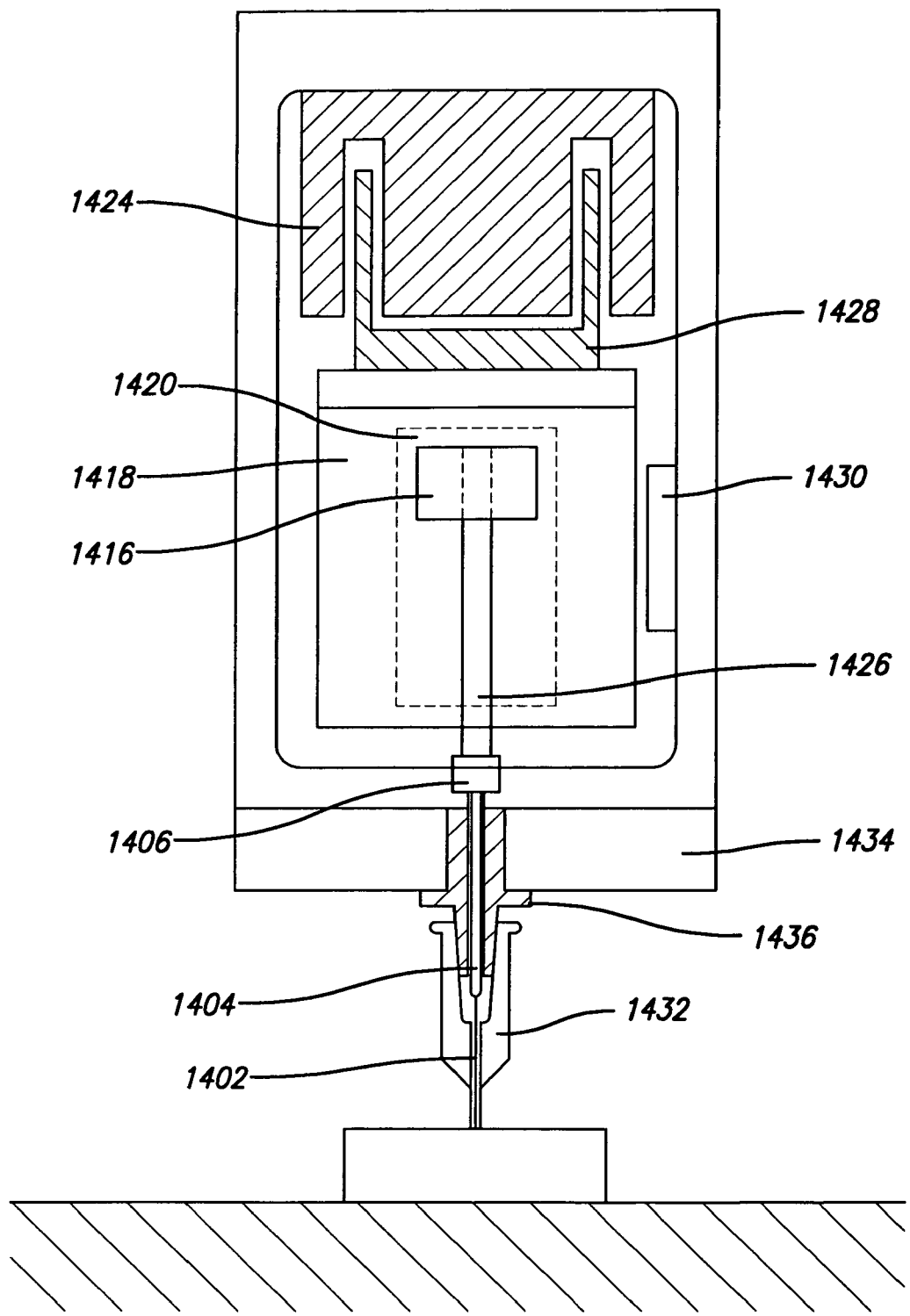

FIGS. 14A and 14B show two embodiments of this invention. These embodiments are based on a commercially available compact positioning system (VCS-10 Voice Coil Linear Stage from Equipment Solutions, Inc.) In the left embodiment the test probe 1402 is held in a mounting pin 1404 which attaches magnetically to a permanent magnet 1406 that is attached to a shaft 1408 on which is mounted an arm 1410 whose motion is detected by the optical position detector 1412. The shaft 1408 continues to a load cell 1414 and then to a support block 1416 that is screwed to the movable platform 1418 of a one axis stage with a guide block 1420 under the platform 1418. The force and motion are generated by a voice coil in magnet structure 1424. In the right embodiment a shaft 1426 is directly mounted in support block 1416. In this case the force is monitored as proportional to the current to the voice coil 1428. In practice this is very close to being an accurate proportionality. If necessary, however, it can be corrected with a correction factor of the moving mass times the acceleration. For example, for a moving mass of 0.1 kg and a maximum acceleration of 100 microns in ten milliseconds, the maximum force correction would be of order) 0.1 kg×100 microns/(0.01 sec)$^2$=0.1 Newton. Since the embodiment in FIG. 14B does not have the compliance of the load cell 1414 to deal with, the motion of the test probe can be monitored using the built in position detector 1430 in the VCS-10 Voice Coil Linear Stage from Equipment Solutions, Inc. Alternately, higher position resolution can be achieved with a high resolution LVDT (for example Measurement Specialties MHR 025) or other supplemental distance detectors such as capacitance sensors, optical beam deflection detectors, or laser interferometers to measure the motion of the movable platform 1418 and thus the test probe 1402 relative to the reference probe 1432, which is stationary relative to the guide block 1420, which is attached to the case 1434 on which the mount 1436 for the reference probe is attached. Thus the body of the LVDT or other distance detector would be fastened to the case 1434 and the core of the LVDT would be attached to the test probe.

This commercial unit can also be used in feedback mode to run the invention with position control. In this case, for example, the force needed to indent the material under test to a fixed maximum depth could be monitored as a function of cycle number. This was not, however, our preferred embodiment because the force and position noise with the VCS-10 Voice Coil Linear Stage and the SCA824 Linear Servo Controller were much larger than in our preferred embodiment. We believe that some of the problem was due to friction in the one axis stage. Feedback can be more easily used with the much smaller friction from flexures such as in the other embodiment shown in this document. We note that feedback control could also be used to run in a force controlled mode.

Figure 15:
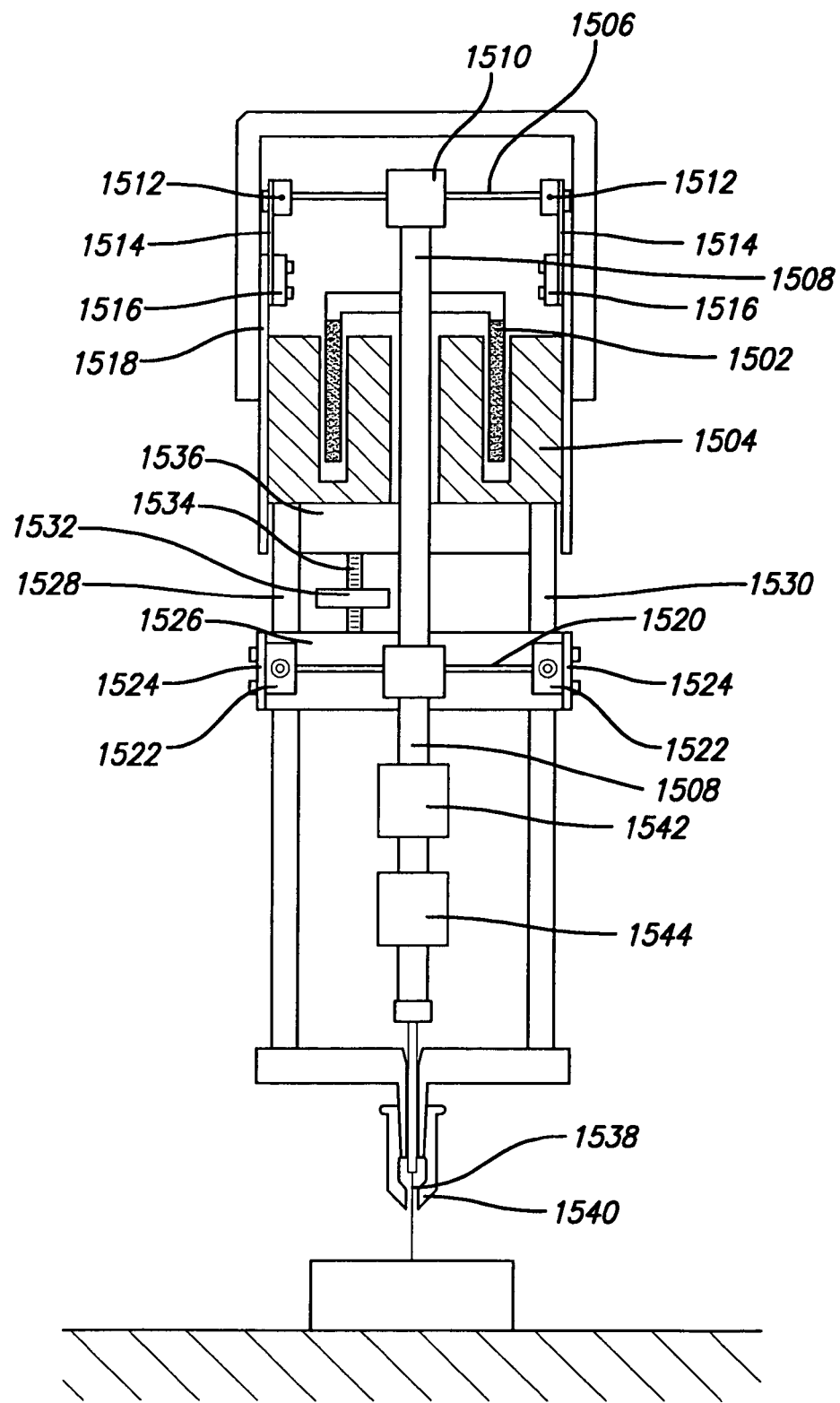
FIG. 15 is a view of the measurement head of this invention in accordance with one embodiment that uses wire flexures rather than the disk flexures of FIGS. 3 and 4 or the plastic flexures of Clark Synthesis force generator shown in FIG. 13.

FIG. 15 shows another previous embodiment of this invention. In this embodiment the flexure support of the voice coil 1502 in the magnet structure 1504 is provided by two wires. The upper wire 1506 attaches to the shaft 1508 with a cylindrical block 1510. The outer ends of the upper wire 1506 are attached to blocks 1512 which are, in turn, mounted on flexures 1514 which are, in turn, mounted, with blocks 1516 to the support shell 1518. The lower wire 1520 attaches to the shaft 1508 with blocks 1522. These blocks 1522 are mounted via flexures 1524 as shown above (as 1514) but rotated 90 degrees around the axis of the lower wire 1520 so the flexures are not as visible as above. These flexures 1524 are mounted on a movable stage 1526 that slides on two rods 1528 and 1530. This movable stage can be moved by turning the knob 1532 which turns the screw 1534 which connects the movable stage 1526 to frame element 1536 which is held stationary relative to the magnet structure 1504 and the rods 1528 and 1530. Thus turning the knob 1532 lowers the shaft 1508 and the test probe 1538 relative to the reference probe 1540. In this embodiment the force sensor 1542 is again a load cell. The position sensor 1544 was optical. A capacitance sensor for position could also be used in this and other embodiments.

Figure 16A:
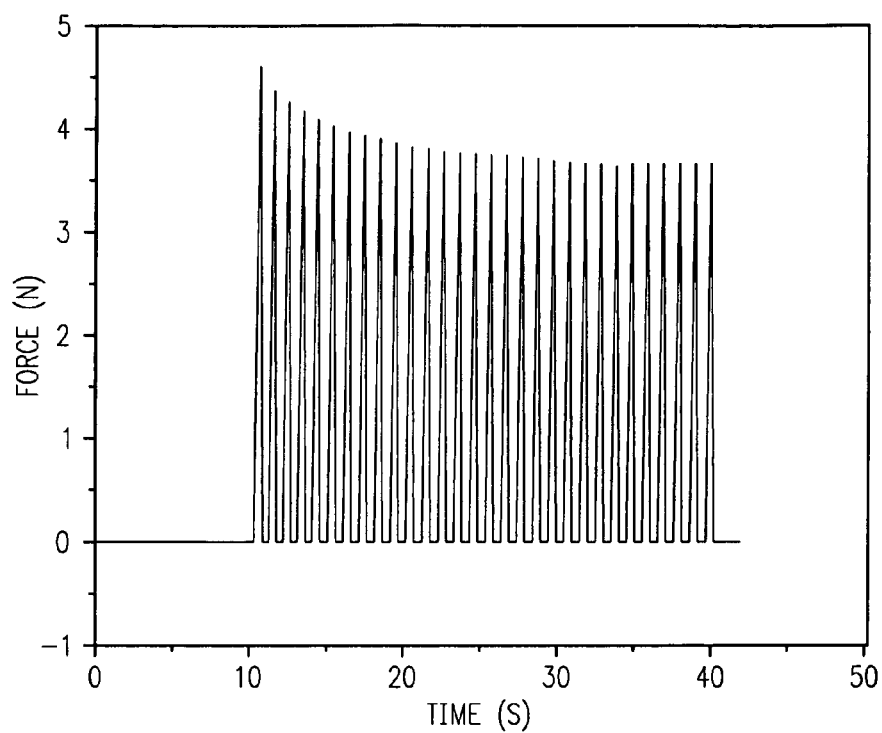
FIGS. 16A-16C show three types of data graphs that can be generated with this invention.
Figure 16B:
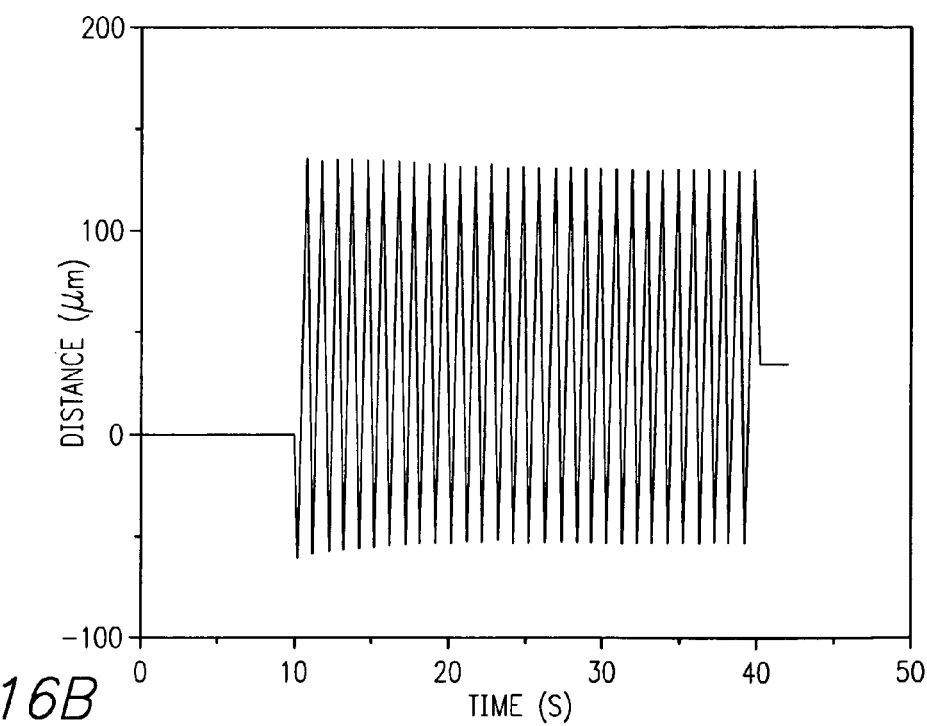
Figure 16C:
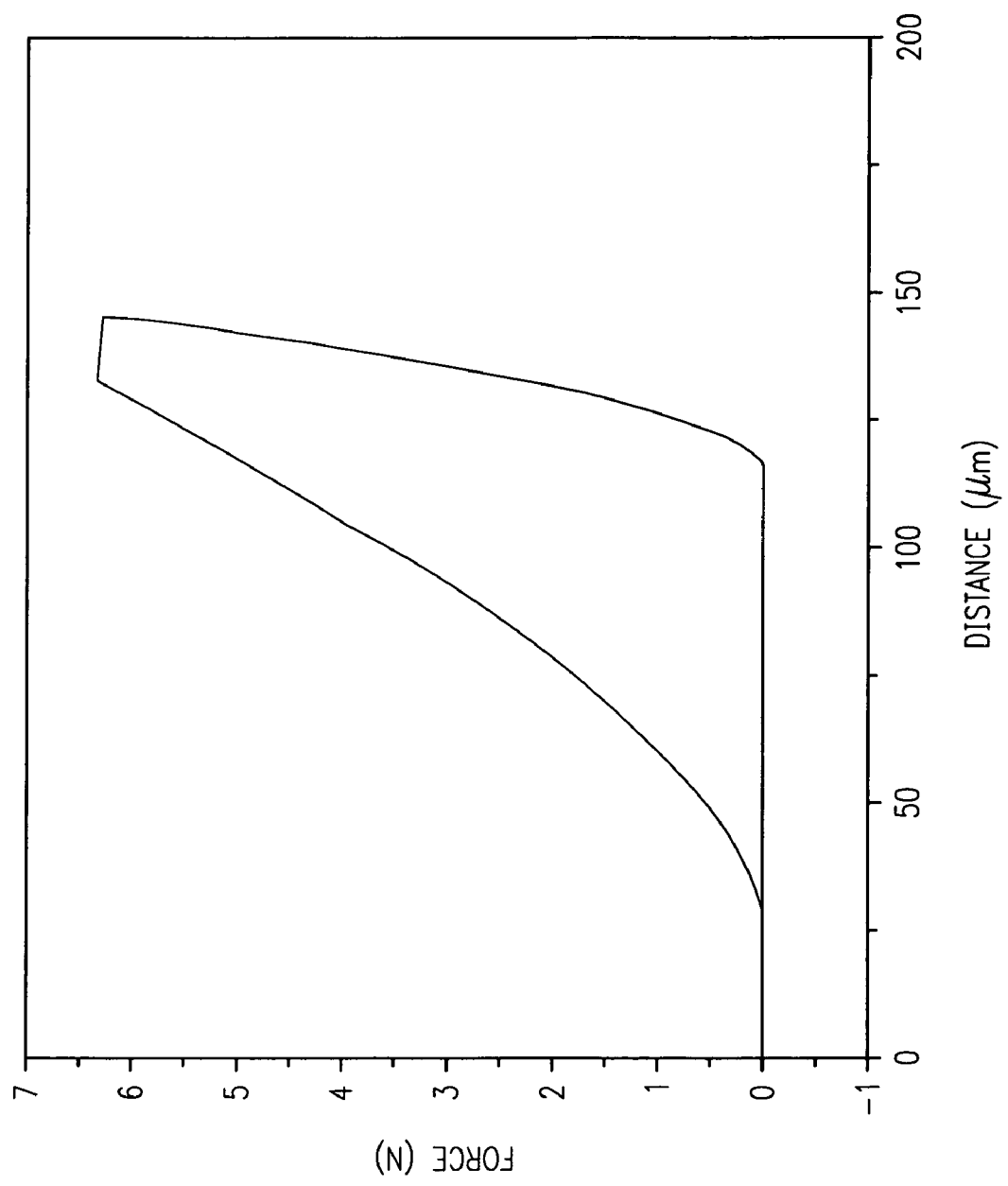

FIG. 16A shows the force measurement for a cyclic indentation cycle test on PMMA taken with the invention as described in FIG. 13. The corresponding distance measurement over the same set of indentation cycles is shown in FIG. 16B. FIG. 16C shows a single indent-retract cycle on PMMA taken with the invention as described in FIG. 15. The loading cycle consists of an indentation at a fixed rate of voltage drive increase to the force generator, a pause at fixed voltage drive to the force generator, and a retraction at a fixed rate of voltage drive decrease to the force generator.

Figure 17A:
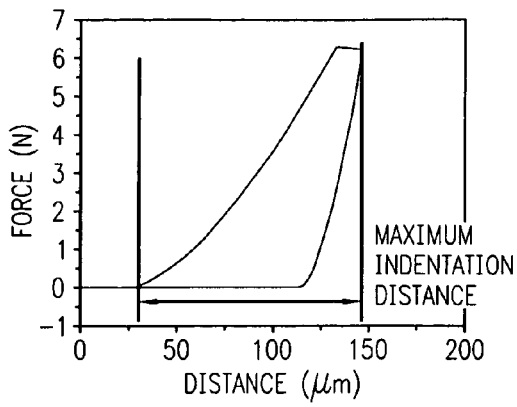
FIGS. 17A-17F show various parameters that can be extracted from data graphs generated with this invention.
Figure 17B:
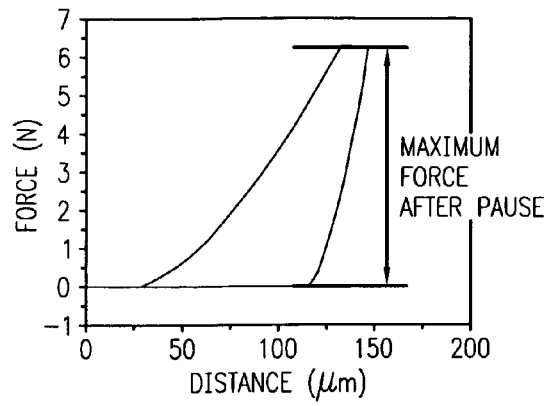
Figure 17C:
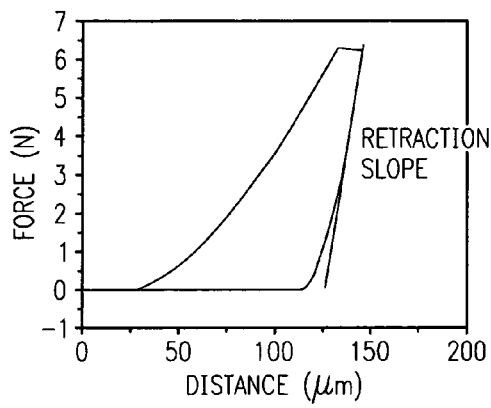
Figure 17D:
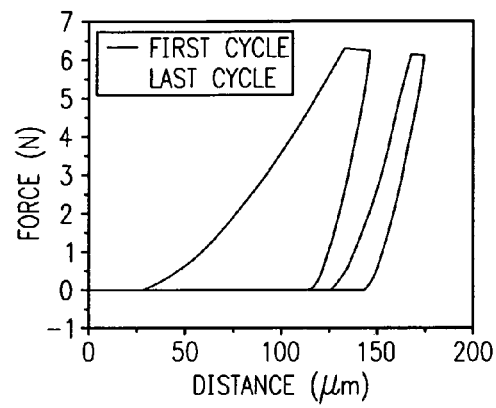
Figure 17E:
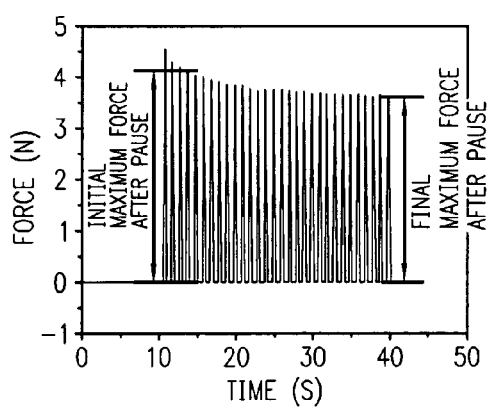
Figure 17F:
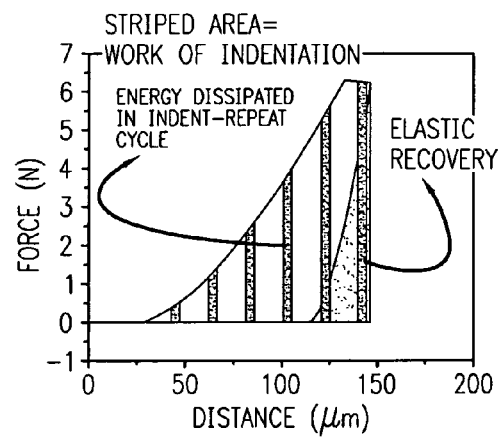

FIG. 17A and FIG. 17B show respectively the measured maximum indentation distance and maximum force after pausing at the maximum drive to the force generator. The pause is included to reduce the effect of viscoelasticity on measurements of the retraction slope and thus the increase the accuracy of the measured elastic modulus. FIG. 17C shows a linear fit to the initial part of the retraction curve, called the retraction slope, which may be used as a material characterization parameter, or in subsequent analysis to determine the elastic modulus of the sample. FIG. 17D shows the first and last indent-retract cycles for a series of several indentations taken with the invention as described in FIG. 15, plotted together for comparison purposes. Change in any measured property over a series of indentation cycles may be measured, as illustrated in FIG. 17E. The change in maximum force is measured between the first and last indentation cycles over a series of 30 cycles. FIG. 17F shows the measurement of work during the indent-retract cycle that may be used to characterize a sample. The area beneath the loading and pause cycle is quantified as the work of indentation. The elastic energy recovery is defined as the area beneath the retraction curve. The difference between the work of indentation and the elastic recovery is defined as the energy dissipated in the indent-retract cycle.

FIG. 18 (prior art) shows the measured parameters that are pertinent to the measurement of elastic modulus and hardness in the invention. The variables and equations used in the calculation are listed. The analysis method used is that of Oliver and Pharr (ref. W. C. Oliver and G. M. Pharr. Measurement of hardness and elastic modulus by instrumented indentation: Advances in understanding and refinements to methodology. J. Mater. Res. 19 (2004), 3. (review article)).

Figure 19:
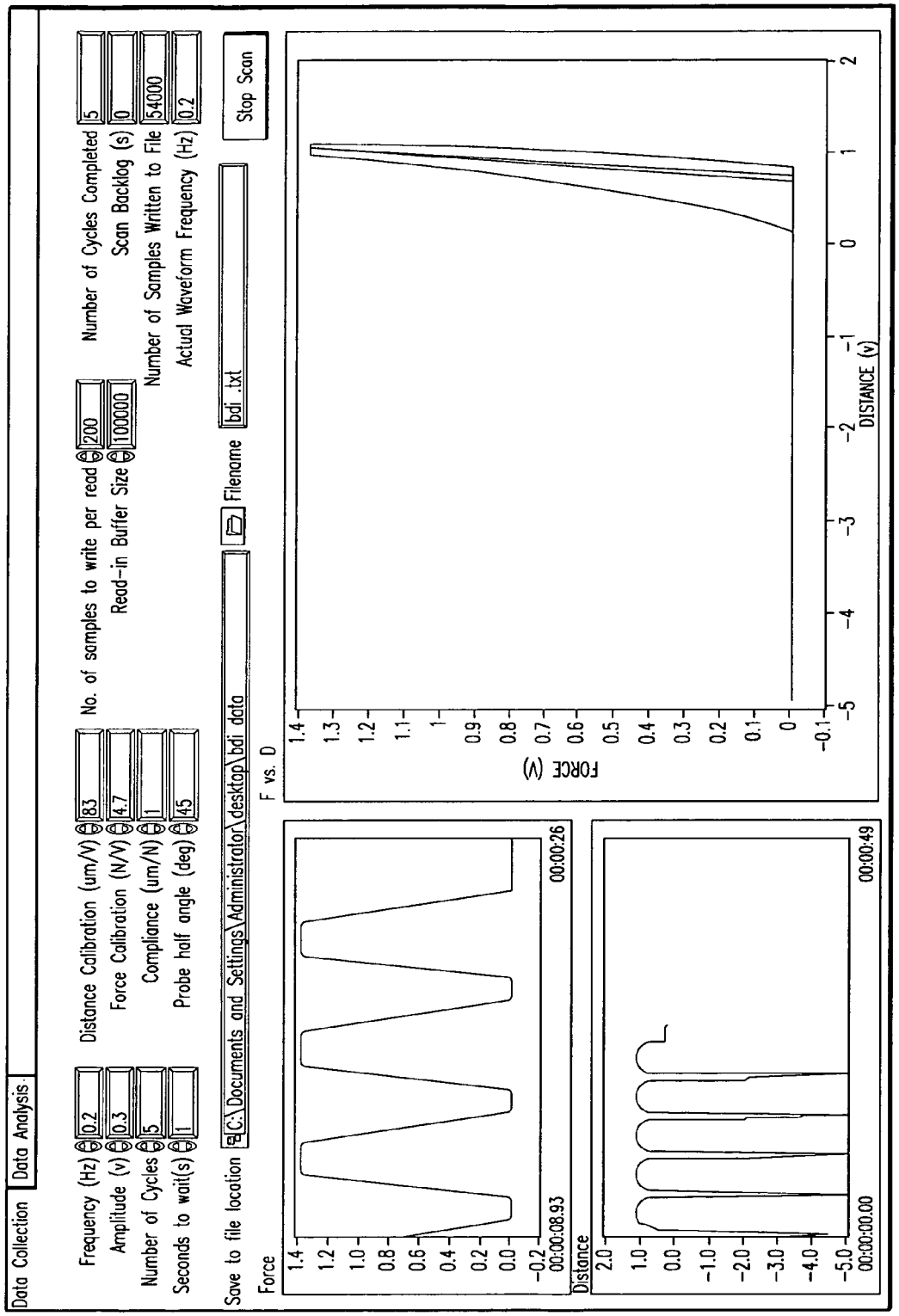
FIG. 19 shows a screenshot of the user interface of the Labview program used in the currently preferred embodiment to control the invention.

The operation of the invention is aided by computer interfacing. FIG. 19 shows a screenshot of the Labview program used to run the invention. The force and distance measurements are collected and plotted both versus time and as a force versus distance graph in real-time. There are several controllable parameters to alter the indentation protocol, including: indentation frequency, indentation amplitude, number of indent cycles, and the half-angle of the conical indenter, called the probe half angle.

Figure 20:
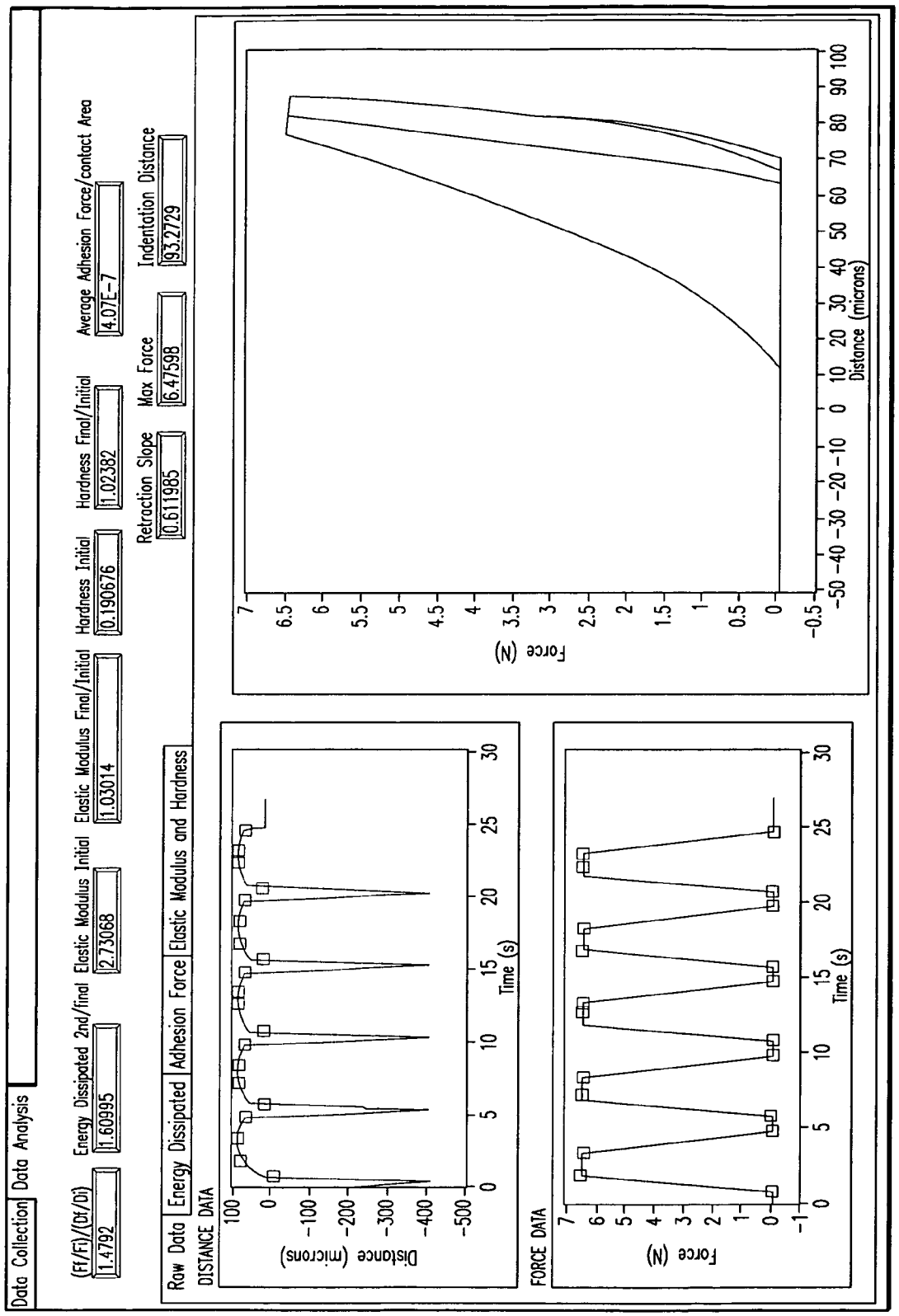
FIG. 20 shows a screenshot of the automated data analysis interface of the Labview program used in the currently preferred embodiment.
Figure 21:
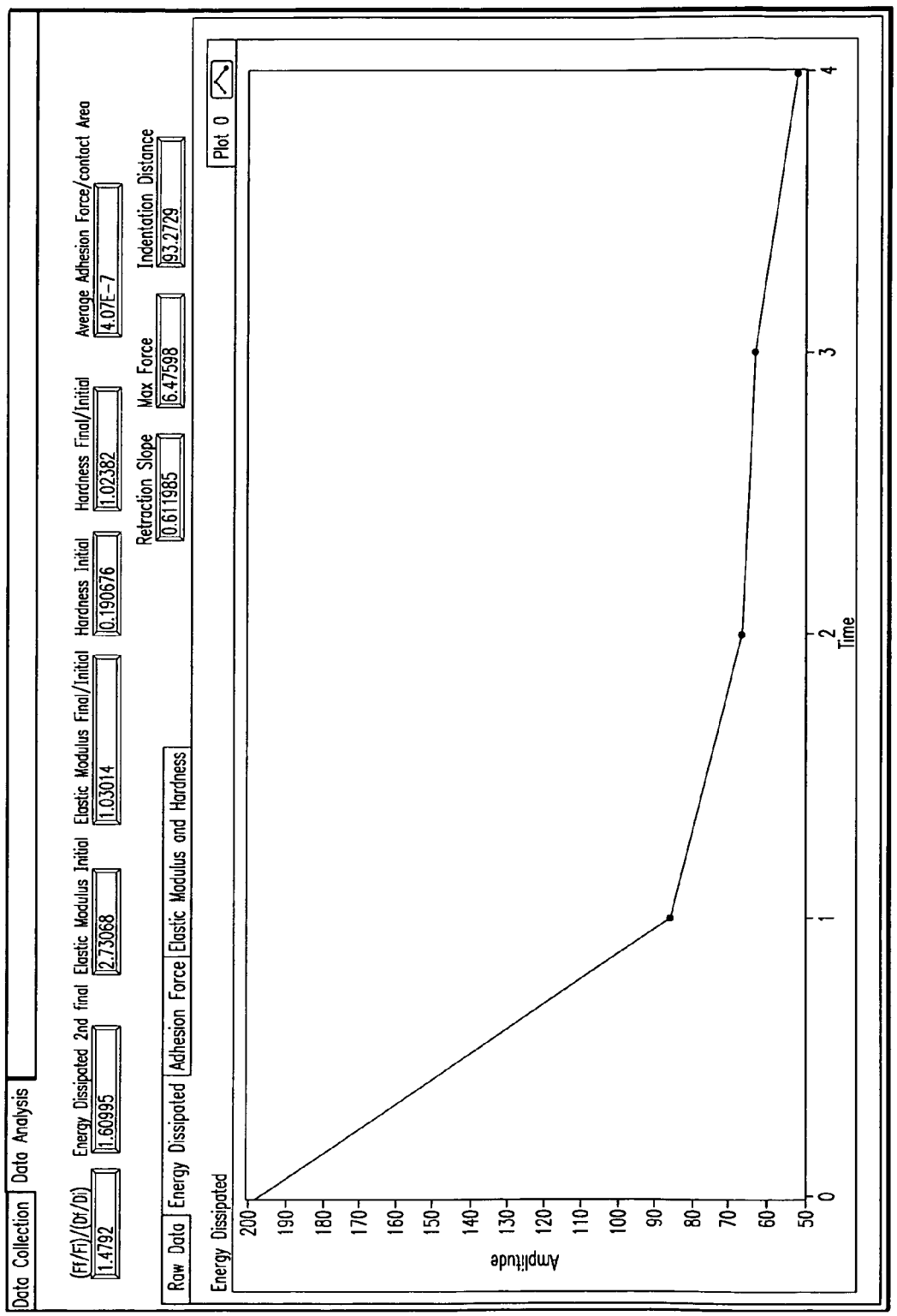
FIG. 21 shows a screenshot of the automated data analysis curve of Energy Dissipated as a function of time from the Labview program used in the currently preferred embodiment.
Figure 22:
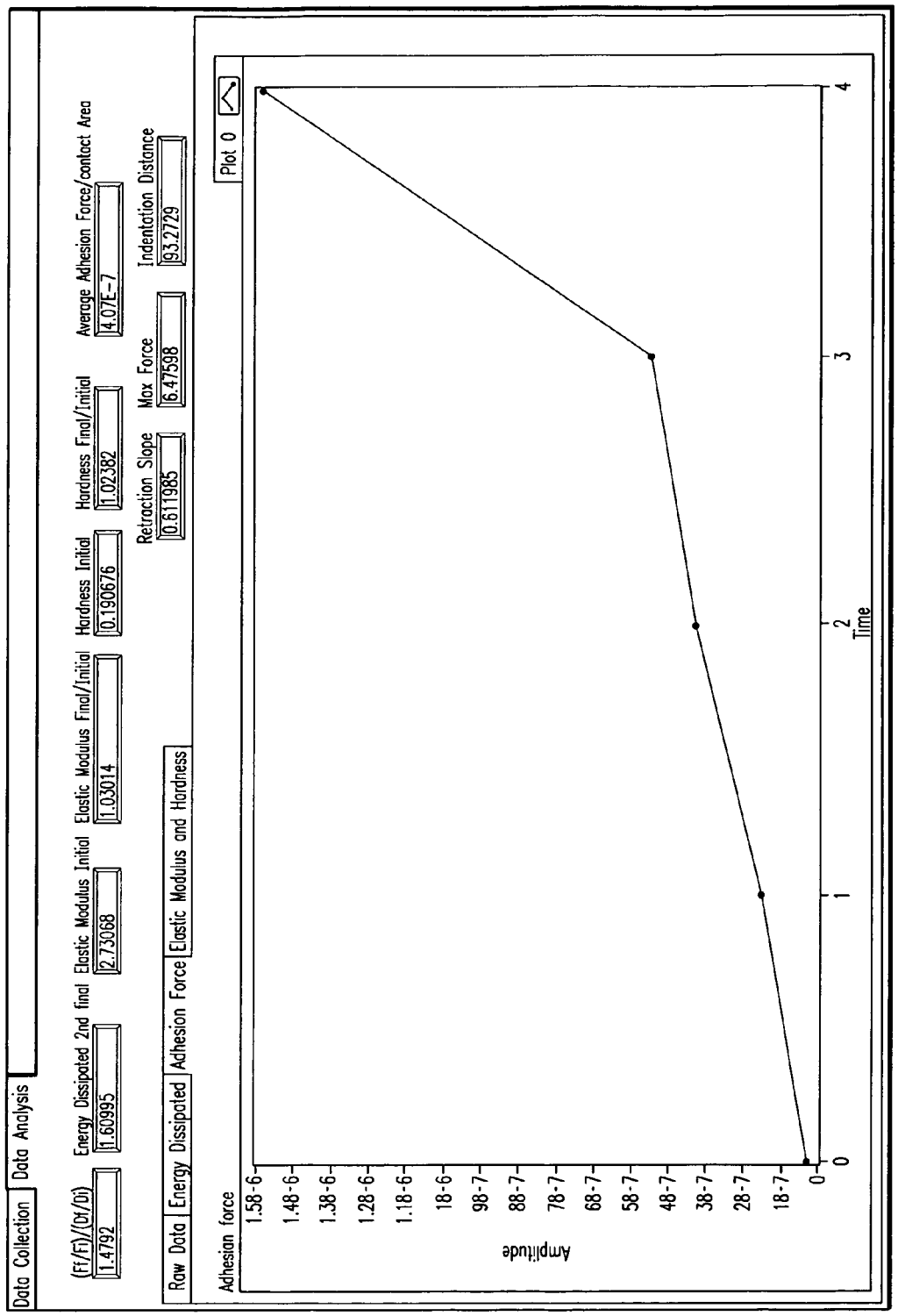
FIG. 22 shows a screenshot of the automated data analysis curve of Adhesion force as a function of time from the Labview program used in the currently preferred embodiment.
Figure 23:
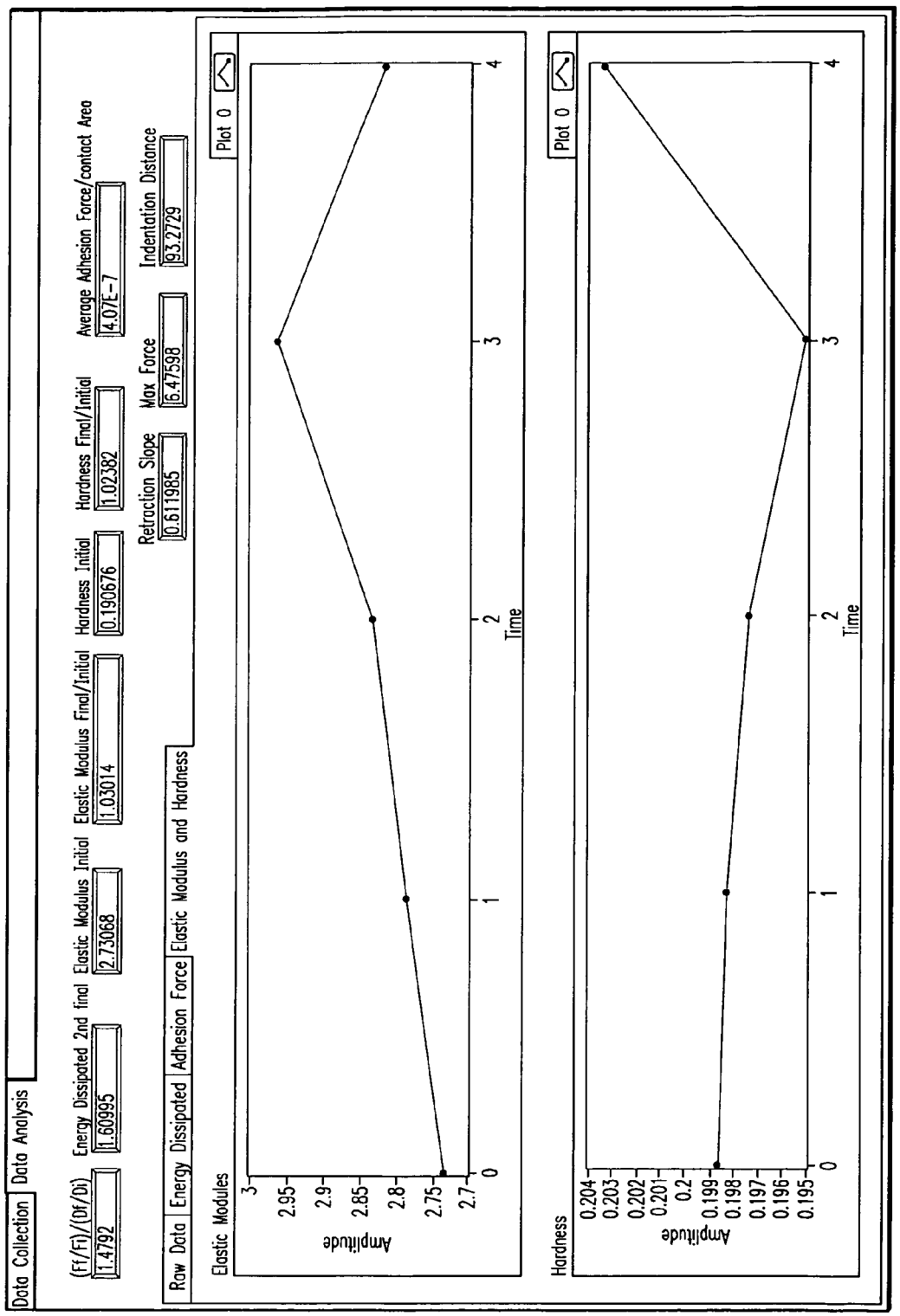
FIG. 23 shows a screenshot of the automated data analysis curves of Elastic Modulus and Hardness as a function of time from the Labview program used in the currently preferred embodiment.

Automated data analysis upon completion of the indentation cycles is achieved through the computer interface. A screenshot of the current data analysis interface is shown in FIG. 20. The main analysis screen shows several measured quantities that may be used to characterize a material, as well as the raw force and distance data, the identified transition points in each indent-retract cycle, and a comparison of the first and last indentation curves for multiple-cycle testing. FIG. 21, FIG. 22 and FIG. 23 show additional analysis screenshots of the change in the measured energy dissipated, the change in maximum adhesion force during retraction, and the change in both elastic modulus and hardness as a function of time through the cyclical test.

Figure 24:
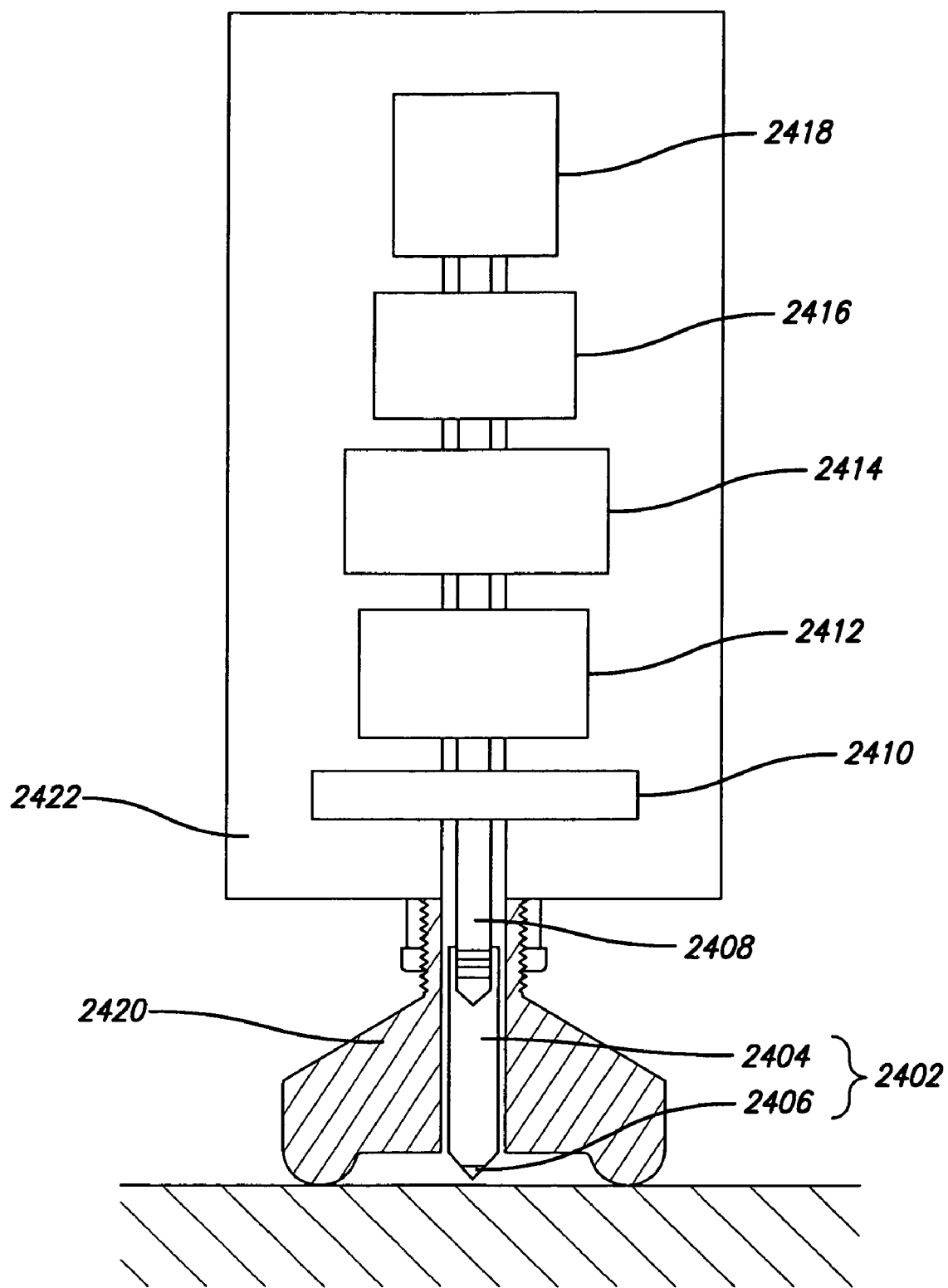
FIG. 24 depicts a generalized measurement head used in the invention.

FIG. 24 shows a generalized measurement head for this invention. The test probe 2402 consisting of a shaft 2404 and a sharp tip (often a diamond) 2406 is attached to a shaft 2408 which is, in turn, connected to an optional torque and angular displacement sensor 2410 then to an optional torque generator 2412, then to an optional linear displacement sensor 2414, then to an optional force sensor 2416, and finally to an optional force generator 2418. The reference probe 2420 is connected to the housing 2422 that holds the transducers and generators. The housing 2422 could be supported and positioned on the sample under test by a support such as those drawn in FIG. 12. The optional torque and angular displacement sensor 2410 together with the optional torque generator 2412 can be used to measure friction with test probes such as 1012, 1022 and 1026 (FIG. 10) or the torque necessary to screw a test probe like 1028 (FIG. 10) in or out of a material under test. This might, for example, be useful in determining whether a patient's bone is suitable for holding screws for mounting orthopedic appliances. With the optional force sensor 2416 and the optional force generator 2418 the force to pull out a screw could be measured as a test of bone quality.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

REFERENCES

The following references are each incorporated herein by reference.

1. W. C. Oliver and G. M. Pharr. Measurement of hardness and elastic modulus by instrumented indentation: Advances in understanding and refinements to methodology. J. Mater. Res. 19 (2004), 3.
2. C. A. J. Putman, H. G. Hansma, H. E. Gaub, and P. K. Hansma, Langmuir 8, 3014 (1992).
3. Briscoe, B. J. and Sebastian, K. S. An analysis of the durometer indentation. Rubber Chemistry and Technology 66 (5): 827-836 1993).
4. James B. Thompson et al., Nature 414, 774, 13 Dec. 2001.
5. Paul K. Hansma, Patricia J. Turner, and Georg E. Fantner, Bone Diagnostic Instrument, REVIEW OF SCIENTIFIC INSTRUMENTS 77, 075105 (2006).
6. U.S. Pat. Nos. 1,770,045, 5,450,745, 5,463,897, 5,473,700, 6,142,010, and 6,405,599, and U.S. Patent Publication Nos. 2002/0170360 and 2005/0262685.
7. U.S. patent application Ser. No. 11/417,494 filed May 3, 2006 titled Methods and Instruments for Assessing Bone Fracture Risk.
8. "Micro Hardness Tester (MHT) for fracture toughness determination of brittle materials", No. 8, July 1998.
9. CSM Indentation Testers, four page brochure.
10. "ASTM Proposed Instrumented Indentation Testing Standard", pages 1-4, October 2003.

The invention claimed is:

1. An instrument for characterizing a material comprising:
    a housing;
    a test probe and a reference probe aligned in the housing, the test probe constructed for insertion into the material to indent the material;
    a force generator;
    a flexure configured to guide the motion of the force generator; and
    a force sensor operatively coupled to the test probe for determining a force versus distance parameter by measuring the force needed to insert the test probe a predetermined distance or as a function of distance into the material.

2. The instrument of claim 1, wherein the force generator comprises a moving coil disposed in a magnetic field assembly.

3. The instrument of claim 1, wherein the reference probe is in the form of a sheath in which the test probe is disposed, the distal end of the reference probe being proximal to a tip of the test probe.

4. The instrument of claim 1, wherein the flexure comprises a first, inner membrane and a second, outer membrane connected to the first, inner membrane.

5. The instrument of claim 4, wherein the first, inner membrane is connected to the second, outer membrane via a ring.

6. The instrument of claim 1, further comprising a distance sensor.

7. The instrument of claim 6, wherein the distance sensor comprises a linear variable differential transformer.

* * * * *